United States Patent
Yoon et al.

(10) Patent No.: US 10,568,917 B2
(45) Date of Patent: Feb. 25, 2020

(54) PASTEURELLA MULTOCIDA BACTERIOPHAGE PAS-MUP-1 AND USE THEREOF FOR INHIBITING PROLIFERATION OF PASTEURELLA MULTOCIDA

(71) Applicant: INTRON BIOTECHNOLOGY, INC., Gyeonggi-do (KR)

(72) Inventors: Seong Jun Yoon, Seoul (KR); Soo Youn Jun, Seoul (KR); Hyoun Rok Paik, Incheon (KR); Jee Soo Son, Seoul (KR); Dong Min Kang, Gyeonggi-do (KR); Sang Hyeon Kang, Seoul (KR)

(73) Assignee: INTRON BIOTECHNOLOGY, INC., Gyeonggi-Do (KR)

( * ) Notice: Subject to any disclaimer, the term of this patent is extended or adjusted under 35 U.S.C. 154(b) by 0 days.

(21) Appl. No.: 16/064,747

(22) PCT Filed: Nov. 10, 2016

(86) PCT No.: PCT/KR2016/012906
§ 371 (c)(1),
(2) Date: Jun. 21, 2018

(87) PCT Pub. No.: WO2017/111306
PCT Pub. Date: Jun. 29, 2017

(65) Prior Publication Data
US 2018/0369300 A1 Dec. 27, 2018

(30) Foreign Application Priority Data
Dec. 21, 2015 (KR) .................. 10-2015-0182593

(51) Int. Cl.
*A61K 39/102* (2006.01)
*A61K 35/76* (2015.01)
(Continued)

(52) U.S. Cl.
CPC .............. *A61K 35/76* (2013.01); *A23K 10/18* (2016.05); *A23K 20/10* (2016.05); *A23K 20/195* (2016.05);
(Continued)

(58) Field of Classification Search
None
See application file for complete search history.

(56) References Cited

U.S. PATENT DOCUMENTS 9,358,258 B2   6/2016  Kim et al.
2004/0241825 A1 12/2004 Mandeville et al.

FOREIGN PATENT DOCUMENTS

EP   1812025 B1    9/2012
KR   10-0818360 B1 4/2008
(Continued)

OTHER PUBLICATIONS

Ahmad et al., "Development of immunization trials against *Pasteurella multocida*," Vaccine 32: 909-917 (Year: 2014).*

(Continued)

*Primary Examiner* — M Franco G Salvoza
(74) *Attorney, Agent, or Firm* — Ballard Spahr LLP

(57) ABSTRACT

The present invention relates to: Myoviridae bacteriophage Pas-MUP-1 (accession number KCTC 12706BP) which has the capability to specifically destroy *Pasteurella multocida*, is characterized by having a genome represented by SEQ ID NO: 1, and is isolated from nature; and a method for preventing and treating *Pasteurella multocida* infections, using a composition containing bacteriophage Pas-MUP-1 as an active ingredient.

2 Claims, 2 Drawing Sheets
Specification includes a Sequence Listing.

(51) Int. Cl.
  *A61K 8/99*    (2017.01)
  *A23K 20/195*  (2016.01)
  *C12N 7/00*    (2006.01)
  *A61Q 17/00*   (2006.01)
  *A23K 10/18*   (2016.01)
  *A23K 50/30*   (2016.01)
  *A23K 50/60*   (2016.01)
  *A61Q 19/10*   (2006.01)
  *A23K 20/10*   (2016.01)
  *A61P 31/04*   (2006.01)

(52) U.S. Cl.
  CPC .............. *A23K 50/30* (2016.05); *A23K 50/60* (2016.05); *A61K 8/99* (2013.01); *A61P 31/04* (2018.01); *A61Q 17/005* (2013.01); *A61Q 19/10* (2013.01); *C12N 7/00* (2013.01); *C12N 2795/10121* (2013.01); *C12N 2795/10132* (2013.01)

(56) References Cited

FOREIGN PATENT DOCUMENTS

| | | |
|---|---|---|
| KR | 10-2012-0076710 A | 7/2012 |
| KR | 10-1260645 B1 | 5/2013 |
| KR | 10-2014-0140698 A | 12/2014 |

OTHER PUBLICATIONS

Palocz et al., "Alternative treatment of serious and mild *Pasteurella multocida* infection in New Zealand White rabbits," BMC Veterinary Research 10: 276 (Year: 2014).*

International Search Report dated Feb. 20, 2017 by the International Searching Authority for Patent Application No. PCT/KR2016/012906, which was filed on Nov. 10, 2016 and published as WO 2017/111306 on Jun. 29, 2017 (Inventor—Yoon et al.; Intron Biotechnology, Inc.) (Original—4 pages; Translation—2 pages).

* cited by examiner

[FIG. 1]
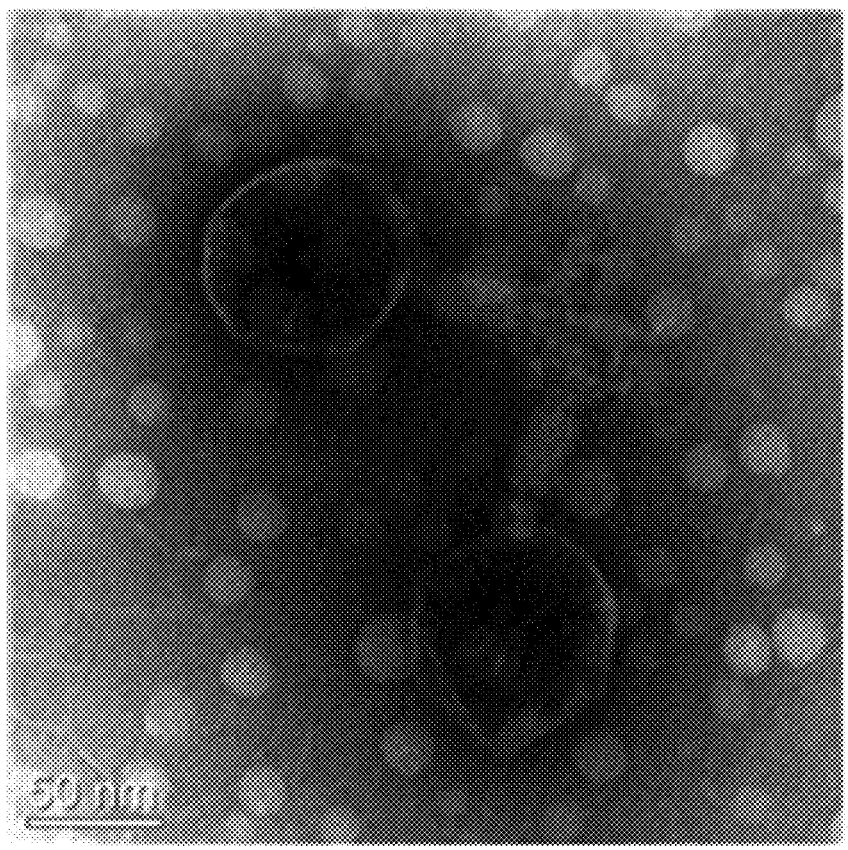

[FIG. 2]
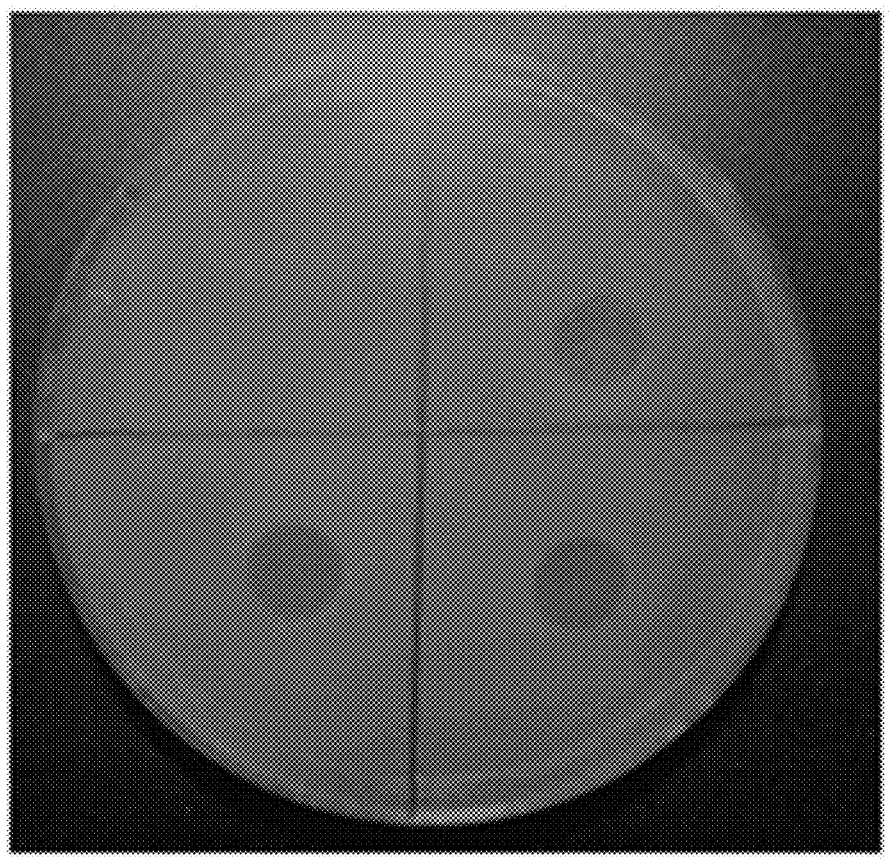

SEQUENCE LISTING

<160> NUMBER OF SEQ ID NOS: 1

<210> SEQ ID NO 1
<211> LENGTH: 39497
<212> TYPE: DNA
<213> ORGANISM: Pasteurella multocida

```
<220> FEATURE:
<221> NAME/KEY: misc_feature
<222> LOCATION: (1)..(39497)
<223> OTHER INFORMATION: Pasteurella Multocida bacteriophage Pas-MUP-1
<220> FEATURE:
<221> NAME/KEY: misc_feature
<222> LOCATION: (5906)..(5906)
<223> OTHER INFORMATION: n is a, c, g, or t
<220> FEATURE:
<221> NAME/KEY: misc_feature
<222> LOCATION: (13329)..(13329)
<223> OTHER INFORMATION: n is a, c, g, or t
<220> FEATURE:
<221> NAME/KEY: misc_feature
<222> LOCATION: (38264)..(38264)
<223> OTHER INFORMATION: n is a, c, g, or t

<400> SEQUENCE: 1
```

| | | | | | |
|---|---|---|---|---|---|
| atgtcatggt | atttgaaatc | tcccttagag | gacgcaggta | tcactgaaat | tagacgtgat | 60 |
| gattcttatc | atgttgacca | cccaatgttg | gaagagttac | agaaaatgga | tgcggaagat | 120 |
| attgtaacat | taaggaacct | tttaggacta | aatgatgact | aaaaagaacc | aagcacagat | 180 |
| gaataaggag | aacatcgggc | tactgaaagg | gaacttcgta | gcctttatgt | ttgttgtctg | 240 |
| ggcagcgcta | ggtctcccta | agcctactaa | atgtcaaatt | gacatggcta | aaacgcttgc | 300 |
| agacacctcc | agaactcgtt | ttatcttaca | agccttccgt | ggtatcggta | aatcttttat | 360 |
| cacctgtgcg | ttcgttgtgt | ggctcctatg | gaacaatcct | caacttaaaa | tcttgattgt | 420 |
| ctccgcttcc | aagcaacgtg | cagatgataa | ctctaccttt | attaagaata | tcatcaacct | 480 |
| attaccttc | ttacacgaac | tgaaaccaca | agctggtcaa | cgtgactcag | ttattgcctt | 540 |
| cgacgtaggt | ggagcgactc | cagaccactc | accttctgtt | aaatcagttg | gtatcactgg | 600 |
| acagttaaca | ggttcccgtg | ctgatattat | catcgcagat | gacgttgaga | ttccatctaa | 660 |
| tagtgccact | cagggtgcca | gagagaaact | atggacacta | gttcaagagt | tcgctgcctt | 720 |
| gattaaacca | ttggaaagtt | ctcgtatcat | ctacttaggg | accccacaga | ccgaaatgac | 780 |
| cctctacaag | gaactggaag | acaatcgtgg | gtattccact | gtgatttatc | ctgccttgta | 840 |
| tcctagaact | aaagaggaag | aactattta | tggtgaccgc | ctagcgaagt | tacttcgaga | 900 |
| tgaatataat | gaaaacccag | agttgcttct | aggtgaaccc | acagacctg | ttcgattcga | 960 |
| taaagaggaa | ctaaggggac | gtgagttaga | gtatggtaaa | gctggtttca | ctttacagtt | 1020 |
| catgcttaat | cctaacttaa | cggatgcagc | aagatacct | ctgagacttc | gtgatttaat | 1080 |
| cgtaggtgac | ctaaacgatt | caaccagtcc | tatggtatac | caatggctcc | cacacgcttc | 1140 |
| taatctcatt | cagtcgcttc | caaatgtggg | tctgaaagga | gacacttacc | acaactggca | 1200 |
| ctcaaccagt | ccccatgtag | gtgaatatac | tcgtaagatt | ctagttattg | accctagtgg | 1260 |
| tcgtggtagc | gatgagacag | gttggtgcat | actttattca | ttgaacggtt | atatcttctt | 1320 |
| aatggataat | ggtggttgta | agatggtta | ttccgatgtg | accctagagt | tcctagcgaa | 1380 |
| gaaagctaag | caatgaaag | ttgacactac | tatcttcgag | agtaactttg | gggacggtat | 1440 |
| gttcggtaag | gtattctcac | ctgtcctctt | aaagcaccat | agatgcgtcc | tagaggagat | 1500 |
| tagagcaaaa | ggacagaaag | aggtacgcat | tattgacact | cttgagccag | tcctctctac | 1560 |
| gcaccgttta | gtggtctcta | aggactgtat | tgatacagac | tacaaaacag | ccgtgaacaa | 1620 |
| cgatggtaaa | catgaagtta | aatattcatt | attctaccaa | ctatcccgta | tcactaaaga | 1680 |
| tagaggagca | ttggctaaag | atgaccgctt | agactcactg | gcattaggtg | tcgaatacct | 1740 |
| taaagaactc | gttaagttaa | acgctgataa | acagcaagag | gagctcatag | aggagttttt | 1800 |

```
agagtcccac atgagcaacc ctattagttc caatgagagc atctctacaa ctctctcagg    1860
aggcgttacg tttatctgga atgaagaaca agatgagttc ggtgtgatta actatttgaa    1920
ctgatagaat gtagcatgac tttaagagaa tacctaagaa attactaaat gtagcataaa    1980
atgtgctaca taaggtggtc ttgagggtgt tctctaagtc attgttttta ttgataaata    2040 actacccac  agtataagag ggagagggag actaaaagtc ttatacagaa agacaacaca    2100
aggagttctc aatgatacat tacattaata tgctacattg agtaagcttg tgtcacaagg    2160
aggtagtgat atgtgaaatt aataattata attataaaag tattattata tgtggtctta    2220
tttattgtat cacttaaaga caaacatcaa ggatacttgg tgttactata tgtactcatg    2280
gtagtccaac tattagtcac ttcgagatga gcaagtggca accataagtc gcttcgagat    2340
gaccaaatgg taaccaaaaa gtaaacacta agacaccttg agtatgccta catagtgtat    2400
cattatgttt acacttggta actcgaagag gtcttaacga aataccacaa aaatctgaga    2460
gaccatctca ttgtgaaaac acccaaagtc ccccccccat agcctcctcc agtcaactca    2520
aagtcaacca atcgtcatcc tttagtcaac caatcgtcat cctttagtca accaatcgtc    2580
tgtgttcata gttactcatc tagtcaacat taagtcaacc tttagttact catctagtta    2640
ctcatctagt caacattaag tcaacccttta gttactcatc tagtcatcca acctttagtt    2700
actcatctag tcagacatct agacctcatc tcttatcttc ttctttatat atagttatca    2760
tttagtttac tatttgttgt tcttctcttc ttctttatcc tcatctactg tcttctatta    2820
ttatattctt atttttttt  ttaatttacc tattgacaac tgtaattatc ttctatatta    2880
tacacctcaa gttaagcgat taacttactt gttcttttaat aaatcagtcg attgaaataa    2940
ttttaaaata attgttgaca agctaaaaag actgatataa tatagacaac aagttaagca    3000
gatagcttac acaatcgttc tttaacaatt tggataacaa aagggttcac tcatagaatc    3060
tctcacaaag agaggtcttt aaataagcat tgagttgata tgcagtgctt atcataaaga    3120
ttaacaacca actagaggaa caaacatgga aagaatcatt aaacaagtgt ttattagtgc    3180
cgagcgtgta aacttatcag acacggataa cgaaatacgt acgtgtagat tagaagatat    3240
cttgtctgca ctgcggtata gattctgtga tggaatagga gctcataaag agaacttatt    3300
tattgtcgaa gtggaatcag ctgcggatat agctgtttta atagctttag cggtaaaatt    3360
tgaacaaaat agtgtgttat tggtggatgc acaaggtgaa gtagctttac agtgtataag    3420
tgaagaagaa gaagaagtag gggatagtgt gtcattaggt tacctgtatt tctcaccgac    3480
caagcccaat gaaaaacaat atatagagat aacaagtggt tatcttgttg cacgataaat    3540
aataaataat caactaatta acagtagagg atatggcaat gagtaaacaa aaaatcagtc    3600
agagagcgtt caaggacgct cacaaattag tcgtgggaat ccgctacggg aaatatccaa    3660
acatcctacg aatccttgag gcgactcact acaacgctag ctcactgggt tggcgttgtg    3720
atatgtactc gctggggtct atgggactcg taactggtta tagttataaa gctcacgtgg    3780
acgtgttcta cgatgagtgg cttaaagaaa agctagcgat tattgagcgt aaatgtttat    3840
ttcgtggtgg cgattatta  catgagttgc aagaggaact actcgaattg ctatggcagt    3900
actatgaatg ggggtactaa tgagcttcat tataacagca aaacatagcg gtctgtggta    3960
cccacctatc tcttacgtct ggtattcaaa gcgagaggct atcagacgct atcgtgacaa    4020
gcacggtata aagggtaagc gaattgaact aaaggtagtc aatgctccac cacttcgata    4080
acaaagagga gtcttttagt agacattaag ttactagtgc ctacactaaa gattcgctta    4140
aacaatgagg aaaacagtta tgttagattt aattaataac cttcgcaatg aaaacgggga    4200
```

-continued

```
actttcagag agcgccatga atttgataga attctttgag agtccagaac acttcgataa    4260
gaacacacat gagcttgtgg agaagacgta tggtcatctt tgcgataagc actacggcta    4320
attaatggga gtacattatg gttaacttat tcttacaggc gcactacgat gatgtcctgt    4380
ctgatattta ttttagatgat ttttttgagtg gcggagatgg ggcgtatgtt ctatttcaac   4440
actacaagta ctgtgtaatc ttcgaagatg agaagacaag tcgtcaacca ttctttaaag    4500
aatacaagct caaccgtatg aagaaagaag acttatgggg tctagttgag aagttagatt    4560
taccatatta tagcggtgag gacatggcgg actatacaaa gtctgatatc atcgatgaac    4620
taatgagtgt tagtaacgaa gagtactacg aaagagctta tgataatctt gactactacg    4680
aactagatta tgattttaca gtgcacggat acaatcaagg tgacgtgctc aaagtagtct    4740
tagtggggtc taaagagttc attaagaaca cttattacac aagagattat ctacaacact    4800
tattcttcga tagtccaatc agagctatgc tgtttgtaac tacggatgaa ggtgtggact    4860
acattgattt aacagagtat ctcaaagact catacactta cgacaaagag gtcttgttga    4920
gtaactttga gcgtacttat gagggtgagc ataaagataa aatctttagc tatctcaaag    4980
agaacttacc gcttgaacta gaatactcat aggggtcttt tatggaactc gaatacctaa    5040
aacattataa aattagattc atgaacacaa cgaacctaac cgacgataat atcaaagaac    5100
tcctttatgt catccgcgat gaagacgtga aggtttact agatactact gacggtggaa    5160
agataactct ttacaactgt gttggaatca ctggacagca tttagttgac ttcattgact    5220
acaatgatta tatagttgcc cgtgtgtacc catacatgaa agagttaggg agaacacaaa    5280
agggctgtct tattggtaaa gctacgttca ctgtacatga agaattatac aacaaggagt    5340
caacgaaatg ttagacgcat atttaagagt gagtgctgac ggttgtcata tcgaactaga    5400
cgcaccaata tgatgagctgt ttgtaacgga gttttcagaa agagcaatca ttaagttgac    5460
taaacgtgac gcagagaagt taattggtcg cttacaagtc aaattaaagg agcttaatgt    5520
cgatgattaa tattacagac ggtctatccg tagatgttcc attcaacaag cccaagtgc    5580
gcttgtgggt gggcggtatg gattcagaag agggctacac atggtttacc caattcttaa    5640
ataaacagga agtggataaa ctaattgaat cattagaaca acttaaatgg gaactagaag    5700
atgaataaaa ataacacaat aaagttagtc acaaaaatga acacaattcg ccaactatta    5760
gaggttggtg gaaaaattga ggcgaagtta tcgccgttaa agggtcgcac tatcgtaaaa    5820
ctggttgggc agaagtcaat agatgaggct gttttcgtaa tgtcaactta aagggtgac    5880
tatcgcattt tcaataagaa aggggngtta ctaacagtac acacactata acaacacgc    5940
acacaatttg aacatttaac aacagccttt gaataggaaa tattatggaa ttcatagaaa    6000
atttaggtca agcgtacgac ctcttagaca cacatttagt tgaccaacag gttgctttgg    6060
aacttgaatc agtcacgttg gggcgtgaaa gattcttaaa gaactatcag acggctatcg    6120
aacaaggaga agtcatctcg aatcctgttg gtaaaaagct tacagaggtc ttgattaaac    6180
gtatggtgga gggtatcaag gcgtatcttg aaaaacattc agggaaagcc cacaaactcc    6240
ctaaagcttt gccgtacatt aaacaaatag acgctgaaaa gctcgcttat attacgatta    6300
aaacggtatt aagcggtcta gtgaaagcga aaggcgacct cccttttatc cagaccgtac    6360
aacgtttgaa ccgcaatgta tttctcgaac tgaaatattc agcagtgcga gaacaggaga    6420
ttgggctttt caaagcttac ctagacgatg gaattaagaa aagggttggt gcctcatata    6480
aagaattgta cgctagaaat gtattagcaa ataatgatat taaggtagaa gtgtatactc    6540
aagaggaaca acaagagggt gtgaacattt acgttggggt cgcactatta gagattctta    6600
```

```
ttgagtcaac aggacttta cagtatcaat cagaagtcaa aaagcgtagt cggggggaaga    6660 ctcttgagca gatgtctttg agtatcgcac ctgaatatgt taatgcactt aatgaccgcg    6720
cagaagaact ggcggactat gctgtcttac atatgcctat ggttatccct cctcgcgctt    6780
ggacgggaat cgacaagggt ggttattata cgttgagcaa agctattatt ccatttgtaa    6840
gagctcgcac caaatcagct atcaaacgat ttaagtacgt tgagatgcct ttagtttatc    6900
aagcggtcaa cattgcacag aatacggctt ggcgcattaa tacgaaagtg ttagacgtta    6960
tcaacgcagt caagaatgag cgtgacccaa tcggttgtat cccaacagct caccttgggg    7020
aaccacctga aaaccatttt gacattgaca cgaacgaaca ggctttaaaa gaatggaaag    7080
aaaaagcagt agaattctat aagtttaggg atactaacat ctcaagacgc ctgcgaatgg    7140
aatcaacgct tcatatcgca gagaagtttg cggagttcga acgcatctac tttccttaca    7200
accttgactg gaggggtcgt gtgtatgcaa ttccttcgtt taatccacaa ggcgatgata    7260
tcatgaaagg ttgtcttatt ttagcagacg gtaaacctat tggggcaaca gggttcaagt    7320
ggttgaaagt acacggtgct aactgtgcag gtgtagataa agtaacattt gaggagcgta    7380
tcgaatgggt agaaagtaac catgttaata ttatggaatc agcccaagac ccagtaaact    7440
accgttggtg gtctgaacaa gagtcaccgt tccagttctt agcgttctgc tttgagtatg    7500
ctaatgtggt tacacagggt ttaggttatg tgtgtagtct tcaagttgct tttgacggct    7560
catgttctgg aactcaacac ttttcagcta tgctacggga tgaagttgga gggaaagctg    7620
taaacttggt gccaagtgat aaagttcagg acatctacaa aatggttgcg gacgtggtta    7680
atactatgtg tgaagaaatg gcggagaatg ggtctgacga tgaattagag gcgcatacag    7740
acgaagaatc gggagagatt acagaacgta tcattcttgg tgacaagtca ttagcgcgcg    7800
aatggttagc ttttggaata actagaagtg tgaccaagcg tcctgtaatg actttatcgt    7860
atggtgcgac caagtttggc tttcgtgacc aaattttaga agacactatt aagccggcga    7920
tgttaagtgg taagccattt cgcaacccta taagtccgc aacatttatg gctgacttgg    7980
tgtggaaagc agttgcgcaa gtggtcgtta agcggtcga ggctatgcac tggctacaaa    8040
aaggtgcgaa gttagtaact aaagaagtga agacaaaaca gacaggtgaa gttttgcgta    8100 atcttgtgc agtatcatgg actacacctg actatttccc tgtgtggcag gagtatttca    8160
aacagaaagc aagtcgtttg gatactatgt tcttagggtc tttcagaatc acaccaagct    8220
acctgcgtgg gactaatgag attgacagtc gtaagcaaga ggcaggcatt gcgccaaact    8280
ttgtgcatag ccaagacgct aatcatttgc gtgcggtcat ccgttggggc tttgagaagt    8340
ataacatcca gtctttcgct ttgattcatg atagctttgg gacaatccct gctgactctg    8400
ataaaatgtt tagatgtatc cgtgagtcaa tggttgacat ctacacaaac aataacgttc    8460
tagagagctt tagaaatgag gtcgaagaac aactacacat tagtcaagtt gaggatttac    8520
cgcgtgtgcc aaaatttggt aagcttgact taaatgatat ttaaaatcc caatttgcat    8580 ttgcttaaaa ggaagcgact atggtaacta ataaatcaat cgttaaaacc aataagaaaa    8640
cacaccgtaa ctactgggaa gaccaagagt ttaaacctaa agggcgtaaa ctaaataaga    8700 caaaagagg tgaatctgat aaatataaat ggtaaatgct acattaaggg aatcgaaagg    8760
ttcccttttt tgttatatgg gtatgctaca aatgaccaga ttataattat attatcagag    8820
ttatgctaca taatattaaa gacactaaag tattgattta aagacaaat taactaccac    8880 acagtataag agaggaacga aataaggtct tactaaaaga ctactaaaag attacactta    8940
aagttaactt aaagattatt attattatgt tatattatta aagaataaat actataagtt    9000
```

```
aactttaagt caaacattaa gacaacttaa agaggattat cattatggaa ttaaaacctt    9060
acaaagcagt taagtattca gaatcttcaa tcactaaaat tttagataag aataaatggc    9120
ttattgctga aacaaagata gatgggatta gaggtctttt agttatcaat aacgaagatg    9180
aacctacatt ctacacacgc acaggacaca ttataaaatg tcttgaaggg gtcttaacga    9240
aagacgattt gttacctttA gttgagtccc gtagtcttct ttatgggtca cagggtctag    9300
tcattgattg tgaacttact gtatctggtg tggacttcta cacaggaagt ggtatcttac    9360
gctctcacag attgtctgaa gggaacttag agtatcatgc aggcgaacct acggatgaac    9420
aatttaagct caagaaagaa ctcttatgcg tccacatttt tggggtcttg cccttactcg    9480
atatgttaga cacagagtca gacattcagg tacaagggtt tatgctacaa gctcactcac    9540
aaatcactgc gaagtcttta ttaggtctta atacgggcat tcagtttaca gtccctgagt    9600
ctatcgaggc gtatagtatg gaagatatta atcattatta taaagaccgt ttagataaag    9660
gctatgaagg gctaatactt aaagacccat caggtattta tagacgcggt aagaaaactg    9720
gctggttcaa aatgaaacca gagaacgaag cagacggaca agtggtagga ctggtttggg    9780
ggtctgtcgg ttcgaaatac gaaagacaag tagtaggctt tgaggtcgaa ctggaagagt    9840
cgggcatggt tgtatcagct tgtaaatatgc ctgaatcgct catggaagaa gttaccgcca    9900
atgtgaaagc taatggtgat tcttattatc taggctacca agtacagatt aagtacatgg    9960
agaagactaa tacaggcact ttaagacacc caagctttga cagattcagg ggtcttgagg   10020
ataaccctca gtctaaatct taactacccc acagtataag agagaaactg ctagacctca   10080
ctccctgttt aacacagtga gggtattata ttattattat tattaagtac tgtgtaaaat   10140
atgtggctac acaaggagga tgcaatggca cattatgatt cagaaatgga tgaatattat   10200
tccaaacgtg aggatgcatt taactctgac ttcacggata aacttgattc ttttcttcta   10260
ggtaaagaca ctatcaaaac tgtcaagaaa ctacatcaat acattcaagg tggtttacct   10320
gctgatgatg tatcttgcta ccgtgcagca cagcaccttg agagagacat taaaaaatta   10380
caaggtgata gaccatttgc ttatgataac aaaggtttaa taaaagtatt aatggtcttt   10440
ctaagtattg cagaatacgt aattaaaaag tatgaagcaa gttgcgttga ttatgctgtt   10500
ggttatataa ctaggaggtg atatgagtaa ctacgcggta ctaaaagagg gagagtatgt   10560
tattatgggt gaaaaacaaa tggaggaata cttaaacaat acaggtattt gccctaatgg   10620
ggatttagga catcatttta aaagtttagc ccaaggtgca tatcttaact tattctcagg   10680
taccaccaaa gataagccaa caaagcctac tggtgcagct gagtctccac aaagtaaaaa   10740
agaagcgact aaggatgttg tcacagaaca agtacaaacg cctagtcact atgctgtctt   10800
tgatggtcaa ggtcaagtac ctaaccttga agccatcgaa gtgattgcac gcaactgtac   10860
gccaagtgag tgggctggtt attgcaaagg taacatctta aagtatcgct tacgggtcgg   10920
taagaaatct agtggcagtc tgtctgactt cgacaagaca cgccaagacc tcatgaaagc   10980
cgataagtat caagaacttt acaagaagct cttaccgtta actatcggtt atactccgtt   11040
ttgacgtacg aagagtgcaa acaatggtgc ttggacaagt ttaatgaagt ctatcaacgg   11100
agtccagcag aagcccagca gtattcagaa atgtatgctg tctgggaaag acgattagaa   11160
tcggaacaaa ggaagaaaca agaatgatta cagcaaaaga agctttacag attcaaacgg   11220
aatctcaaaa ggtaatctta gaccactaa agtacattga agaacggatt ctagaagcag   11280
ccagtcaagg tgatttgtct ttagtaatcc gaaaggagcc ttataatagt tttatgaagt   11340
acgctaataa aacagcccag tctgttgtta aatctttaca agaacgtggc ttcttagtat   11400
```

```
atgaatacta caaagaaaag cattttggtg cagatacagg tctttgtatt gagtggagta   11460
acccttgtgt ctaaatggta taatgtaatt attgagtcta agactacacg gtcagacgtt   11520
gagatgtacg cccaaagtct tgagaaagct ttagagcgag cggaaaatag ggctaagaat   11580
cttaccgtag ccacagggc tgaacacgaa gtaacacggg tagcattaaa ggttactcac    11640
ggtacaacta agtgaaacta aggagaatt attaaacatg gcaaaacgac aaacatatac    11700
agtagcagtc acaggtgttg gtacggtagg ggactacccg tacatcgcta aaccagattt   11760
tggcacaggc agttttaagt ctgcgcatgg taactataaa ttcacattga ttatggataa   11820
agaagaccct aaatgtattc aactcatgaa ccttattgat gaggaatatg aagaaaattt   11880
agaaaatctt cgtgcggacc ttaacaattc ctcagctaaa caagttcgtg gtaagaaacc   11940
acctaagatt gaagagggag ataaaccata ttttgacaat gaggatggaa cagtcacttt   12000
caaattagca tgtcacgctg ggttcactga taagaagaca ggtgaagccc gtaagattaa   12060
cttaccagtg acagacacaa aaggaacagt attgaagaat gtaccaaaca ttggtgcaaa   12120
ctctgaggtc aaagtgaaag tgcaattagt tccttatggt tcaactgctt tccctgcgtc   12180
tattaaactt cgtccactgg ctgttatgtt ggtcaagtta gtagagtatg gtgcgcaagg   12240
cgatacctta gattggggtg atgaagaagt cgagggaggt tatatagccc aagatgatga   12300
cactaggtct ccagtgaatc tagatgaaga tatcccattt ggtgatgatg aagattcaga   12360
gaacggggac ttctagtaat gagaaaccct aagttcacag cacgtcgaac tggggtattt   12420
cgctcaggtt tggagtcgac tgtaagtaaa cagttggaat caagaggtat agcatacgag   12480
tatgagcaat ggcaagttcc gtatgttgta ccagcttcaa aacatattta tacacctgac   12540
ttcctattac caaatggaat cttcattgag actaaaggtt tatgggaagc agatgataga   12600
aaaaaacatt tattgattcg agagcaatac ccagaactag acattagatt ggtgtttagt   12660
aatagtaaca ctaagattta caaagggtca ccaacaagct acgctgaatg gtgtgagaaa   12720
cacaatatca agtttgcgga taagaccatc cctatagcat ggttgcgtga gggtaaacaa   12780
gagatagact tctcgaaact aaagaaagct aagactaaaa ggagaagtga tggcgaaagt   12840
acaatttaaa acaagggaga taacttcata tattatcgtc cattgtagcg caacccgtcc   12900
tagtcaagat attgatgtgc ggacgcttcg acagtggcat aaggaacgtg gttatttaga   12960
tgtaggttat catttaatta ttaaacgcga tgggacagta gaagaagggc gtatcatctc   13020
acaaattggt gcacacacaa aaggatacaa tgcggtctca gttggtgtat gtctagtcgg   13080
tggtgtagat gaaaatatgc aaccagaatc taacttcact gaggctcaaa agttgcact    13140 aaaagaagta ctggaagacc tcaaagctaa gtatccacac gcacagatta aggtcacaa    13200 tgactttgcg cctaaagctt gcccaagttt taaggtatca gaatatttac agacgggtga   13260
aatgaagacc tttaaaggat aatacaggag ataacatggt ggactcagag gagacctcag   13320
aatttttana tgtaggttat catttaatta ttaaacgcga tgggacagta gaagaagggc   13380
gtatcatctc acaaattggt gcacacacaa aaggatacaa tgcggtctca gttggtgtat   13440
gtctagttgg tggtgtagat gaaagtatgc aaccagaatc taacttcacg gaagctcaaa   13500
aagttgcact aaaagaaata ctggaagacc tcaaagctaa atatccacac gcacagatta   13560 aggtcacaa tgactttgcg cctaaggctt gcccaagttt taaggtatca aaatatttac    13620
agacgggtga aatgaaaacc tttaaaggat aatacaggag ataacatggt ggactcagag   13680
gagacctcag aatttttata tcacacacac tgtgagaact gtgggagtac ggacgcaaat   13740
tctgtttact ctgatgggca cacctttgt tttgcctgta ataccacagt taaaggagat    13800
```

```
gaccagcgtg tagagaagaa acataatcac aacaagaaga aagagaaagg ggtctgggat    13860
tttactgaat ataacggtag gtattcagca ctcacaaaaa gaggtatctc agaggctact    13920
tgtaggaaag ctgaatactg gattgcaaca acacagtctg gtgatatttt acaagtggca    13980
aactaccgcg accaatcagg gacactcgta tcacagaagt tacggggtaa ggacaaagag    14040
tttaagacga caggtaaaca ctctaaagag tctttgttcc tgaagcattt atggaatggt    14100
ggtaagaaaa tagtcgtcac agaaggtgaa atagacgccc tcacagtaat ggaattacag    14160
caatgtaagt atcctgtggt atcattaggc aacggggcga gttcagccag acaaacttta    14220
agtgcaaatt ttgattatct agaccagttt gagcaaatta ccttatgtt tgatatggat    14280 gacgctggtc gaaaagcagt ggaagaagct gcaccagtat taccagctgg taaagcctat    14340
gtagcagtcc tgccactaaa agatgccaat gagtgccaca ttaatggaca atccaaagcg    14400
gtaatcgacc agatatttaa tgctaacaag tggattccag acggtgtgct agcagctaac    14460
cttttaaaag aaaaagtgaa gcacacatta gagtctgagg aatcggtggg tatcctttt    14520 gataaacatc cgaccttaaa tgagaagacc ctaggcgcac gtggtggcga ggtcattatg    14580
gtgacttctg gtagtggtat gggtaaatcc acatgggtaa gacaacaagc agtcgcttgg    14640
ggcaatcaag gctatagaat tggtcttgca atgctcgagg agaaagtaga gaaaccatt    14700 atagacttat tgggcatcaa caacgcagta agactacgac aggataacga cctaaagaaa    14760
caagttgtcg ctgatggtcg cttcgaaaaa tggtttgatg agttgtttgg gaatgacaac    14820
tttcatctct acgattcttt tgctgaagca gaagtagata ggctacttag taagctagct    14880
tatatgagaa acgtcttgg gtgtgatgtt attatcttag accacatctc aattgtagtc    14940
tcagcatctg aagagtcaga tgagaggaag atgattgata gcttatgac taaactcaaa    15000 tcatttgcta aagctactgg tgttgtcctt gtgactgttt gtcaccttaa gaacccagat    15060
aagggtaaag ctcatgagga agggagagct attagtatca cagacctgcg aggttcaggg    15120
gcattaagac aacttagtga tactattatt ggcctcgaac ggaaccaaca aggtgagaac    15180
ccaaatgagg taacggtacg cttattaaaa tgtaggttca caggtgatac tggtgtagct    15240
ggcactgttt tatatgataa acaaacaggt ctattgagcc agctagaaaa actaccgac    15300 tctattgact tctctgacga ttacacacag gagttctaat gtttattctt tatattatgg    15360
tcgcaataac agcagcactg atgtttatc acactgtctt ttatggacta ccaagtcaaa    15420
acgacagctt tcgtgcattt ttggaagctg agaaacaaat taacgatatc aaggagaaat    15480
cgaatgttaa aatcactcac taaatactta gtcaaaatct ccatcgcatt attaactttt    15540
gcagcgaaac ataatgaccg caaggcacgc ttgaagatga atgttattgg tcgaactgag    15600
cgattaatcg aaggtttaaa cgctaagctt gaagcagaca ccaagaaact tcaagaccgt    15660
aaagaacaac ttgaagcaaa actaaaagct gaaaagcagg aaacgtttga ccaagcacac    15720
aactacgcgg aggaagcagc aagtttaatc tcatcagctc aacgcttaaa aggtaactta    15780 tgattaaaatt aaaacgacac gcaacgatag gacttacaga cactattgat gcctacgaac    15840
gcaaaatcca cattaatact ttaggtgaca agtgacgtt agtgtttcgt tggcggtctc    15900
gctcagatgg taaacgacac actcagcgca caacgttacc acctagtacc gcaatattat    15960
tagcaaatca gcttatggtt acttcaacat tagcaggcac aaccaccaag tagccttta    16020 gtagtcactc gattactagt ggctacaata aagattacta aaggagacaa gatgattatt    16080
tctgatattg aagcgaatgg tttattagac acggtaagta agttccattg cgcagttact    16140
tatgatacag caacaggaga gaccaagaag tatcgaccta ctgatttcga agtgtaccta    16200
```

```
agagaccttg agaaagtggt aacagctgac ggcttagtga ctttccataa tggttataag    16260
tacgatattc aagcattaaa tatcctagcg aagcagtatg gaattaaatg gtctggtgtt    16320
ccacaacgta attctatcga cacacttgtt ttgtctcgcc ttatttattc agacatcaaa    16380
gacagagaca tgggtctgct acggtcaggt aagattcaag gcacacactt tgggtctcat    16440
ggtcttgaag cttggggcta ccgattaggt gaaatgaaag gtgagtacaa gtatgacttc    16500
aaggagcgta ttgagtctga aggtgaagaa tacattgcag gtatggaatg gaacacttc     16560 tcagaggaaa tgttagaata taacgttcaa gatgtagtgg tcacaacgaa acttatggaa    16620
cgcttgatgg ctcacaagtg gtattcctct aaggtagagg gtttcgactg gaagacttgc    16680
aatgctgatg atttttggtc gtcacatggt cattcattta cccttgaaca tgaagcagcg    16740
tggttgttaa gtaaacaaga acgtaacggt ttccctttttg accgtaaagg tattgagaca   16800
ctttacattg agttgtcatc gaaacgggca gagctaaccc agaagttagt agaaatgttc    16860
ggttcatggt atcgaccaaa aggtggtaaa gagttcttca aacaccctaa aactggtgtg    16920
gaattagtta aatatcctaa agtcatctac ccgaaaactg gtagtatgtt cctcaaacca    16980
aagaacaaag cacagcgaga gggtagaaaa cctttagaaa aatcaaagac gccttacatt    17040
aaaggttgtc cttatacacc agtagaacac gtcacgttta atccaagtag tcgtgagcat    17100
atcgcattga agcttcaaga agctggttgg actcctaccg agtttacaga caaaggggcg    17160
ccagtcgtca atgatgagac acttgattca gttatcgtag atgaccctaa gaaacaggca    17220
gctatcgatt taattaagga atacttaatg attcagaagc gaatcggaca ggtagctgaa    17280
ggtgacaaag catggctcaa gtacgaccaa aatgggtaca ttcatggtag tgtaaatcca    17340
aatggtgctg taactggtcg agcaacacat agcttcccta acctcgcaca gattcctagt    17400
gcacctcacg ataagcaagg aaacccaatc atgggtctta ctggtaagta tggtgtggaa    17460
tgtcgcatgg cttttggcgc tgaacatcac aaagggtctg atggtaaagc ctggattcaa    17520
gttggaacag acgctagtgg tttagaactt agatgtttgg gtcactacat gtatcctttc    17580
gataacggag agtatattga tgttatcctt gaaggtgata tccataccaa aaaccaaata    17640
gctgctggac tacccaccag agacaatgct aagacattta tttatggttt cctttatgga    17700 gcagggacg ctaagattgg tgagattgta caaggtacag cagctgatgg taaacgtctc    17760
aaagctaagt tcttggagaa tacgccagca atcaagatgt tacgtgatag tatcaccaat    17820
gcgcttgtag ctgaatctaa gtgggtgggt aaccagaaca ttattaaatg gaaacgtaga    17880
tatattaaag gtctagatgg tcgcatggtt cacatccgta gctcacactc agctttaaac    17940
actttactgc aatcagcagg tgcgttgatt tgtaaagagt ggatagttga agtagagaaa    18000
ctattactag ctagtggtct taaacatggt tgggatggag atttttgctta tatggcttgg    18060 gtacacgacg aaatccaagt ggcttgtagg acacaagaag tagccgaaaa ggtcgcagat    18120
atatcccaac aagctatgag aaatgtacag aacttttata actttagatg ccaattagac    18180
acagagtcta agattggtcg aaactgggct gagtgccact aaggagacaa aatggaaaag    18240
aaagacaaca aaccgtggaa tcgtgatatt actatcaagt tttcacttgt atatccagag    18300 aacactttg atattgcgaa tctagtccct gatgaagaag ctaagaaatt actgattgag    18360
tgcatcaaaa cttatattgc acctccacag ttcctacata tcttgaaat tgaaatgatt    18420 gacccaactg ttggtgagaa gaagaccaca agaaaacta aaggcaaggt aaaagataat    18480
gaatgagtat ttaagctttt tacagttcgt taaagtaaat gtggtgacat tcaaaagtaa    18540
ctacgcacgg aacaatgcag ggctcattgc ggaagcagca tcacgctatc atatcacttg    18600
```

```
cttaaatgct aacggtagaa actgtggaca ttgggtcttg actaactctg ggtctaactt   18660
tttatatgaa aatggaggtt gccaatgagt acaccaacat ggtttaaaca accctttgag   18720
tcaactttcg atgaagaata taaacatcga gtcaatgaaa tcatcttgga tgcagtaagt   18780
cacacaggtt ttcgacttta ttgggttgaa gtatctgaag aaatttcaga actttacgaa   18840
gaagtaaacg accattttat gaacggtgtg acgccagaag aatttaataa gtggttgtat   18900
cccttaattg tggatgctgt cttattccta ccattcaaca aagacgggga gtttgaacaa   18960
tggtaaaatt cttaaagacg cttgtaaagg atgcattaat gtatgtggct atgttgttca   19020 tgttttcat aacattagcc cacatttgca tcccattttt aatcgttgta gctttagtta   19080
aattcatcat gtaaggagaa attatgccag ataaaatttt agtatcacgt ccaatgttag   19140
aagaattagt gaattgtaag atagagctcc tagcattacg gcacggtggt gtagatgact   19200
gggaatggta ctgcgaagct ttcagtaatt tcatcgaaca ccaatttcca gatgacgttt   19260
tagatgtaga aacaggtttt gatatcttag ttggtcgtga aattgataaa ctggagaaac   19320
tccagcatga agtttaacct taatgaactc aaggaccacc taaagccatc taagaaccta   19380
ctagtcctcg atggggactg gttggtcttc caagcgatgt ctgcctcaga acaagaagtg   19440
gactggggga atgatatatg gacattaacg tgtgaccacg ctaacgcatt agatatctta   19500
cagaactcaa ttgaagcttg gactaccaga cgctcaactt ggaagaacgc tacaatcgta   19560
gttactttct ctgatgatac aaactggcga aaagacctag tggatgagaa ctataaggct   19620
aaccgtaaga agactcgcaa accttgtgga tatcgacatt tcgttgatac ttacatggaa   19680
cgtgaagata ctatttgtgt ggtacaccct aatctcgaag cggacgactg tatgggaatt   19740
attgggtctg gtggtcatca tttcggtact caaaaggtaa ctcttattag tatcgataag   19800
gacttccgaa cagttcctaa ttgtgatttc ttgtggtgtt caacaaataa catcctacct   19860
caagaccaag agtcagcaga cttctggcac ctatatcaga caattaaagg tgatatcact   19920
gatggttatt ccggtattaa aggttggggt gagaaagcag aagactttct tttagacccct   19980 tatatgttgg ttcgccaaga aagcaccttg caatctggta agaacaaagg acaacttaaa   20040
gtccagtatg tgaaagcaga taaaggtgat aattccttat gggattgtat cgtatcgttg   20100
gggtctaaag ttgatatgtc tgaggaagat attatcaaac aagctcgaat ggctcgaatc   20160
ctccgttaca gtgattatga ctttaagaat caacaagtta tcttatggac accagataaa   20220
ctgaaccagt gaataactac cccacagtat aagaggggaa tactaaagga gaccaaatga   20280
tttccacaaa agtagaacgc gatgcatacg ctagggaatt attaaatagc cctaacaaaa   20340
tccctagaat cccaatggaa ctagttgtca tcttagagta tctagcagac cctattaacg   20400
atgattgggg gctaccacca gagcttaaag agttatctaa gaattcttat ggtggttatg   20460
tcttggggtg ccagattatg cttagacatc ttcatcggtt gtatgcatta caaaataata   20520
aatataattt tgatgaggag gattaatgtg tttttaaacct aaaatcccta agatggactt   20580
accgaacaaa cctattgacc cagcaccgct aactgccaca cctactgggg ttgcctttgg   20640
tgaacaatct gatgacaaag ttgaagaagt tggacgtaag acactcaagg tcggtaataa   20700
attagcaggt aaaatcaaag caggaggtaa gtaatgggct ggaacccagt taaaagtatt   20760
agaaaggctg ctaaaagcgt aggtaaagcc cttcgtagaa ctattaaaag tgttgcaaca   20820
ccagttgctg gtctttagg agctaaacct caagacccac aagatgtagc cccaccgcct   20880
ccaccagctg tccaagtggc tccgccaact tctggtgagt tgaaaaggga atcactgag    20940 gatactgaaa gtgggcgtaa gaaagcagcg tctcgtggta agcgtagtct acaagtaact   21000
```

```
agaacaagcg acaggggat taatatttaa ttatggctaa ttcaacagtt aaacgtgagg    21060
gtacgttagc tgaagaaggt gcagaggtaa tctacaagcg tttagagaac gataggaaac    21120
cttatgagac tcgtgcggaa agttgcgcaa aggtaaccat tccttcaatt ttcccgaaag    21180
agtctgataa cgactcgaca aactatcaga caccttatca atcggtaggc gcaaggggtc    21240
taaacaacct cgcttccaaa ttgatgcttg cactctttcc gatgcagact tggtttaaac    21300
tgagtgtgtc agaatttgtt gctaagaaga tgactggtga taatgaaaca cagctaaatg    21360
aggtcaacac aggtctcgct atggttgaac gtgttctcat gaattacata gaagctaata    21420
gttatcgggt tgtactcttt gaggctctaa aacagcttgt agtctctggc aacgcccttc    21480
tttatgtaac agacccacgg gagtcaggta ataataccta caacccttta aaactctaca    21540
agttaaacaa atttgtagta caacgtgaca cttatggtaa tgtcctccag attataacta    21600
aagactctat cgcctattca gctctaccag aagacatcag aagttcgatg actaaagacg    21660
gtgagcataa gccagatgaa cagattgatt tatatactca tatttatctc gatgaggaat    21720
caaatactta tcagaaatat gaagaaatag acggtgaagt tatctctggg acagaagctg    21780
agtatcctat cgacgcttgc ccatttattc cagttcgtat ggttcgccta gacggagagt    21840
cttatggtcg ttcttattgc gaggaataca tcggagacct caattcatta gagagcctca    21900
ctaaggcgat tattgagatg tcagcaatta gtgccaaagt ggtcttctta gttaacccag    21960
cagggatgac tcaaccacgt aagctaaaca agcgaagaa cggtgatttt gttacaggtc    22020
ttccaacgga tgtgactgct ttccaagtag ataaacgctt ggatttctca atcactaagc    22080
agacagctga tagcattgag gcacgcttag ggtttgcctt tatgttaaac tcagcggttc    22140
aacgtacagg tgagcgagtg acagccgaag agattcgcta tgtggcgtca gaattagaag    22200
ataccttagg tggtgtttat tctattttaa gtcaagagct acaaatgcct ctcgtaaagg    22260
ttctcttgaa acaacttcaa gcaaccgcta agattccaga gctaccaaaa gaagcaatcg    22320
aaccgactgt atctactggt ctggaagcac taggtcgtgg tcaagacttc gataagttgt    22380
cccaatgttt agcagcttgg tctcaagtgg ctaacctagc tcaagaccca gacttaaaca    22440
ttcgcaacat taaggaacgt attgcaacgt caattggtat tgataccaca ggtatcctat    22500
tgacagacca agagaagcaa gaaatgttgg ctcaacaggc agccgaacag gcgactatgg    22560
gtggcgcaca gtcactaggc gctggtgctg gggcattagc tacaagttca ccagaagtag    22620
ctgcgcaagc tatggataca gctggaatgg aagcagttta aataaaggag actaaatgaa    22680
taacgcagaa gtatatgcca gtcttggagc tggtaatgca gtaattacct cacaggatga    22740
acatgaggaa gcaatgttag ctttagatgt agcagtccgt gatggtgatg acctaattag    22800
tgtagctaaa gatgaagaag gttatgggtc ttttgaagaa gatgagaata accaacgcgt    22860
cttagtgaac tctgaaggtg aacaagaaga taccgaagga gaaccagctg agtctggggg    22920
tggtgaggaa ctacctgaaa tcggagagac cccagaaggt cttacgaata tctcagcgga    22980
actaaaagaa aacatcgacg gtttctatga gatggctcaa ggtgctattg acaagggctt    23040
acttacagat gagcaaatca gctctttctt agatgaatat gaagaaaaag gtacattgtc    23100
agaagacgtc ctaaataagt tagaggaagc tggttttact aaagctttcg ttaagtcgta    23160
cattaagggt caagaagccc tagcaaataa atatgaacaa caaatttatg actatgctgg    23220
tggaaaggat aactacgcta agattatggg acatcttcaa gcggagaacc ccgccctcat    23280
tgagtctttt gttaaagcag taaacgacca cgacttacag accattcagg gtatcttaaa    23340
gtcagctcgt gattccgcta gtcgtaagta tggaaaacca gctgagcgtt cagtcgccaa    23400
```

```
gaaagcggtg gcgcaaccac aaagccaacc tcaagagact aaaggttttg cttctcgaga   23460
tgagatggtg aaagctatgt ctgataaacg ttatggtcgc gataaagcat atactgacga   23520
agtagtgcgt aaagtagccc taatgaagta attattatta ttaatcaaaa caaggagaat   23580
taatttatgg gaaatgttgt tggacagcaa atgggtgcag acgctggtaa gggtcaatca   23640
gcatcagaca aactagcact attcttaaaa gtatttggtg gtgaagtaat cactgctttt   23700
gaacgtaact ctgtgactaa tggtcgccat attgtacgcc aaatcagttc tggtaaatcg   23760
gctcagttcc cagttcttgg tcgaacctca gcacattatt tacaagctgg tgaaagctta   23820
gatgacaaac gtgttggtat caagcatact gaacgcacta tcactatcga tggtctctta   23880
actgcggatg tgttaatctt tgacatcgaa gatgcaatga accattttga cgttaaatct   23940
gaatacacca agcaattagg cgaatcttta gcgattgcag cggacggtgc tgtattagcg   24000
gaattagcca aagcttgtaa cttaacatct aacgatgaaa acattgccga tcttggagca   24060
ccttctgtcc taacaattgg taataaatct actttagata caccagttaa actcggtaaa   24120
gctatcattg aatatttaac acaagctcga gcaaaattga cctctaatta tgtaccgtct   24180
ggtgatcgtg tgttctatac aaccccagac aactactcag ctattcttgc agcgttaatg   24240
ccagatgctg ctaactacca agcttttaatc aacccagaaa ctggtgcgat tagcaacgta   24300
atgggctttg aggtcgttga agttccacat ttattagtgg gtggtggttc agatgacaaa   24360
gcaggcaccc aaactaaaca cgtcttccca gcatctggtg gtaaagtgaa caagactaac   24420
gttgttggtt tattccatca ccgcacagct gttggtactg ttaagttgaa agacctagcg   24480
ttagaacgcg ctcgtcgttc agaatatcaa gcagaccaaa ttattgccaa gtatgcaatc   24540
ggtcacgggt atttacgccc agaagcctta ggtgccttag tgtactctgg ttaataaaca   24600
gctagccatc cttaggtcaa ctttgggtgg ctatttttc tcccctttat aaataaggag   24660
acgcaatgca acaggattta agtataacca caagtgttga ccttgaagct gttaaccaga   24720
tgcttagtgc gattggggaa tcagctgtct ctactttaga cggtgaagct aatgcagatg   24780
tggcgaacgc taagcgactt ctaaatgaag ctaaccgaga gattcaatcc aaaggttgga   24840
cttttaacac atacgaacaa gaaacattac taccagatgt cttagtggt cttatcccat   24900 atagcagtga ctatttactt ttaatgacaa gtggaacaag gactccctat gtgaaccgtg   24960
ggggatacgt ttatgattca gtctcaaaga ccgatgtgtt tcctagtggt atcgttgtag   25020
atatcattaa gttacaacca cttgatgaga tgccagaacc ttttagacgc ctaatcatta   25080
agacagcaag tcgaaggtta aatcagcgat tctttggcgc accagaagtt gacgctgcgt   25140
tacaagagga aatcgcaaag gctactattg actgtaatat ttatgaagta gattatggaa   25200
gctacaatgg tattcagggc gataacttca ttaatggtct tctagcgagg taataagtat   25260
gccactatat agccaaagta ttaagaattt aaaaagtggt atcagccaac agccagagat   25320
tttaaaatat ccagaacaag gtaaccaaca aattaatggg tggtctagtg aaatcgcagg   25380
gttacaaaag agacctccta ttatcttcaa tcgtatgctt ggtcgtaaag gtctctatgg   25440
ggacgctccg ttcattcatt taattaatcg tgatgaacat gagagatact acgctatctt   25500
cactgggtct gaaatcaagg tgattggtct tgatggggca ccttatgtag tcaaaggaaa   25560
tttctcttat gtgcaaacaa ataacccacg caaagacctc cgaatgatta cagtcgctga   25620
ttatactttc gtagttaata cttcaaaggt aatcaaagag gacacctcaa gaatctacc   25680 agacttcaat gagaagcaag atgctttgat aaatgttcga ggtggacaat atgggagaac   25740
tctcattgta ggttttaacg gtgcagaaca agcaaaatat ttgattccaa acggggataa   25800
```

-continued

```
accagaacac gttaagaaca ctgactctca atttattgct gaggaattag ccaaacaaat   25860
gagagaaaag ttaccaacat ggacgtttac tgttggtcaa ggctacattc acattcaagc   25920
accacaaggc acatccattg ataatcttta tacgaaagat gggtatgcag accaattgtt   25980
aaaccctgtg acccattatg tccagacgtt aataagtta cctttagtgg caccagatgg    26040
ctacatggtg aagattgttg gtgatacctc gaagacagcc gatagttatt acgttaagta   26100
tagcgcagcc aagaaggtgt gggcagagac tttaggttgg gatacaccta aagggttcct   26160
tgataataca atgcctcata ctttagttcg tgagtcagac ggtacattct catttaaagt   26220
ccatgagtgg aaacagagac ggtgtggtga tgaagacaca aacccactac cgtctttcgt   26280
agatagttct attacagata tcttcttcta ccgtaaccga ctaggttttc ttagtggtga   26340
gaacgtgatc ctaagtagga catcacgtta cttcgacttc ttcccagcta gtgtagcaaa   26400
taattcagat gatgaccta ttgatgtagc aattagtcat aataggatta gcaaccttaa    26460
atttgcggta ccatttagcg aggagttatt attgtggtct gatgaagctc agtttacact   26520
gaggtcttca agtatactct cagctcgaac cattgagtta aacttagtga ccgagtttga   26580
tgtgagcgac caagcaagac cgtttggtat tggtcgtggt atttactttg cgaacccacg   26640
aagcacattt acgtctatca gtcggtatta tgcggtacaa gacgtatcga gtgtgcgtaa   26700
tgctgaggat atgacagccc atgtccctaa ctatatccca aatggggtct ttagtattca   26760
tgggtctaac acagagaact tctgtacggt gcttactaag ggtgctccaa gtaagatttt   26820
catatacaaa tacttatata cggatgagca attactccaa cagtcttggt cacattggga   26880
tttaggtggg gagtgcacta tcttggcttg tacaactatt ggtagtaaga tgacgattat   26940
atttgagaat caacataatg tgttcatagg gacagtaaga ttcacaagag acatcaagga   27000
cttcccacag gagccttata ggtctcattt agacttaaag acccttttaca cgattccaac   27060 cgataaatat aatatcacaa cgaacatcac acggattcgt ctagctgata tttataacag   27120
tgcaagattc acaagaggta aagtcacctt aatgggtgtt gatggtcgaa actttgagtt   27180
ccaaccgaaa gaggacttct gggcatctga cgacactatg gacttacaag gggattactc   27240
tgggcaacaa ttcgtagttg gtttcaacat tccgtttact tatgagttcg ctaagttctt   27300
aattaagaaa acggataaag atgggtcgat gaccaccgaa gatatcggca ggttacaact   27360
acggagagcg tgggttaact acgaggaatc tgggcattc aatgtgaggg tcgttcatgg    27420
ttcaactagt tttaactatg aaatggcagg gtctaggttg gggtctaggg aacttcgtat   27480
tggcgaattg aatattagca cagaccagtt caggttccct gttacaggta atgctttaca   27540
cacacaagtc ttcttactta gtgactcacc aacaccacta aacattatcg gttgtggttg   27600
ggaaggtagc tatatccgaa gaagtagagc tatttaacaa taacaataag gaggtcatta   27660
aatgactatg caaattcaaa aagttgacaa agggttctca tttagtgact tccgcttatc   27720
taaatgggat aaactagaaa aaagagcctt aggtcaacca atggtatcac ctgaggaact   27780
tgatgcagcc cttgataaaa actcatattg ccttgtgcat gatacattaa ggtatctggc   27840
agtaggtggg gtgactcctg agggtggtat ttggttccta acgtctcata agttgacaa    27900 gctgacacca gctgaacgct taagatgtt catgctcctt aaaagacacc taaaagctgt    27960
taagttgaaa ttcaaagata cgattcaaga cttctataat atttgtgtgga ttcttaacta  28020 tcctcacatt tccttattga agttacttgg tgctaagttt gagtattcct tgcctattca   28080
ctcacctaaa actggggagg tctttttatca attcactatc cagaatgaat actacacggg   28140
ggattcggaa tgtgtgaacc aacaacgcta actatggctg ccctctcagc tacctcaatg   28200
```

```
gctgcgtctg ctgctgcttc taccaaagct caagctggta tgattacagc tcagcgtaag    28260
aacgctatcg ccatgatgaa gaaagctaac atggataatg ctaacgcaag gttacaacaa    28320
gttgacaaag cggaggcagc tagacaccag atgactgagc ttaatttaga taagttacag    28380
actcttggca cccttaacac agcaataggg gaaagcggtc ttgagggtcg cagtatggat    28440
agactcaaga acaccacaga gagtgaatat attcgtaaat cccgtaatgt cactgagaac    28500
tatgagcgtg actatgcgtc tctacacgca caaatgttag gaacgtctct aagcactcac    28560
gacaacatta agacacttca atcccaagag ccttctaaag gagctagagc attgtctggt    28620
gttgccagtg cattgcaggt cggtgctggt gcgtatagta tttataaagg aggtaagtaa    28680
tggctagtaa gattgaagca gccttaggga acagacctca actagggtct gagggtctcc    28740
acgttaggga gggtatgcaa tataaccctc aatcaaccca gcacgttgac cattactcag    28800
atagcattaa acgtctgatt ggagtcgctg attgggctaa aggagaaatc cagaaggaag    28860
ttgaagttga ccaatctgac ttcttactta caattacac agctgaacaa cgacaaaaac    28920
ttagtgagca aggggtctta ttaacacaac acaataagaa gaccgttcag aattactata    28980
agaaacttgg taatctagct gcctatgatg ctgacaaagc agtaaaagct ttaattgatg    29040
acggtaagat tacaaaccgt aaggaactca ctgaaacact catggaaatc cgaaagtcaa    29100
ccatgcaagc ttatgctcaa gtgaatggat ttgattttaa cgaacaagac ttccaactag    29160
gttttgctgg taatgtagta aacgtgata tcaccctttt tgatggacta gcagtaaaga    29220
cctcaaatcg cttagattca caaattgtca ccaattcggt ctctgatatt aaacgtatcg    29280
tgaatgacag tgagtttggg acaccagcag tcttccctaa ggtcttctct gagtatctaa    29340
ccaacagctt atctaacgag tcaatcccta acccacgtat ggctcgtgag attggggcgc    29400
agacactaaa tgacctagcg gacgctgata acggtcttcc acttcttctt agtctcaagg    29460
attacaaagt aactctcgat ggggtcacta agtcttggag agaccatgta ggtggagatg    29520
cttgggatac tttagaaaac aaagcccgaa caaaaactac tgagcgttcc actggtatgt    29580
tgtcacaact tcaagttgac attacagcat ccgctgggag accgatagaa gacgctgaga    29640
aactattgga aacttataat caacgattca atcggatgta cccagaggaa cattccaatc    29700
cagctaggtc tattctaact aattttgctg tccatattca acagcgtaag aataaggaag    29760
cgactgatgc taaactagaa gccgataaag cgttagtcaa acaacaaaac ttccttaaat    29820
attctgacgc tattcagcga gctaagtctg gtgagattgt agatttgaac aacttaggat    29880
tctctaagga tgaacaaatt gaattctcac agatgattct agagaaactt gagaacgacc    29940
ctaatatgtc acctgaacag aaagtaaaag agttcgcttc gttacttcaa gttgaccata    30000 agaatgagc tttccgtagt caatttgata cacttgttgg taatgcccaa tctgacatcc    30060
aagctgcggt cattaatggt acatgggacg aagataaggc tcaagcgttc cagcgtctaa    30120
cagctttgta caaagtcaat gcgcctctgg ttacactctt agccccagaa agtgctgatg    30180
tgattgccac tatggattta cttgataaat ataaagtaga gccacaaagc ttaatcgacc    30240
agatgaaagc aaacaagggt ctctcacagg tggacaaaga gattcgagat aggacctggg    30300
aaactcaaaa acagcagtct aagaatccat tattctctta tatgtctggt tcaactgaaa    30360
gggctgcccg agtttatttt gacagctact tcctaaagac tggcgatgaa aaagcagcct    30420
tcgaggcgac aaagcagttt cttgaagcaa caacctttga tgtaggtaaa tctagttggt    30480
ttaacattaa ttctagggac agagttgggt ctattcccaa ggcacaactt atggttactg    30540
atgacccaaa cagttggaag gaaggtggtg agattcttaa tgaagccatt gagttaatca    30600
```

```
agttcggtaa aatcttaggt aaagactctt tagatgatgt caaggtggct aaacctattg   30660
gtacccaagt gattgtcacc tatacccccac aaggtattaa tgtgctaaac ttagatacta   30720
attacaataa gacttttaca caggaagact tgcgtaaggc tttcatgaag aaacaagaag   30780
aagccttaaa agtagccgaa aaggttaaga aagaaaagca agataagttc tttaatgatt   30840
acgaagataa tcgtaagaac aaaccctttcg accctaattc aagttgggga ggataattaa   30900
ggagaacaga tgagtaaatt cgatattaac gctgattcag gatatgaaga gtatttccag   30960
aaggcgtcac aacaacatgg gatacccttta gacctcctaa agaaaatttc atggattgaa   31020
tctagataca acccagatgc tagaagtcct actggggcta ctggtatcat gcagttcact   31080
aaagctactg gtcgagctat gggtcttcgt atcgacggtc aggttgatga gcgaagagac   31140
ccatctaaag ccatcgatgc agcagcaaga catatttcag acctctataa gaaatatgat   31200
ggggattatt ctttaattgg tcttgaatat aaccaaggtg caggcaagct aggtgaacca   31260
caactagaag ccttcaggggc tgggcgactc aatgaggtct ctgaggaagg gcggaagtac   31320
attgagttac tcacggataa gcaaatatct aacacgggggg tcttaaatga ccctctaggt   31380
gctaacgctg atgggactgg tattacaccc ttatcaccac ccattaagtt tactgaaggt   31440 gataccttttc agacacccga agttaccaac agtaagctat acacaatggg aatccttaat   31500
cctgatgaac acaaaacaac accttaccgt tcattctacg gggatgagcc acaggaagtt   31560
ggtatgttcg atggaacatg ggacgccatt aaagcatcag ctggtaatac aatcatcgga   31620
aacctagtta ccacagcagt caatactagc ggtgattttg acggtcttga taatacccttt   31680 ggtaaacaag gtacttatgc tttctcgaaa gaggaagaag cccagattcg caaggacgta   31740
aatgtagatt accttaatgt catcgcaggt gctaatagcg cagaggattt acaagctcga   31800
attaagttag ctaaggaaaa tgaagagaga gacagagctt taggtcaaac tggtattggt   31860
gcacaacttg ttgctggttt agccacagcg cctttagacc ctacaacatg gattccagta   31920
gctggtgcat gggctaagtc tggtacgctt attaagaaag ctgcgtctgt tggcctccaa   31980
gctggtgcat ggaacgcagt tagcgaagac attagaacag cagtagttgg cggagacact   32040
aattatagta tggcttttcat gggaggtgct ttgtttggtg gtagtatgac agcacttgct   32100
cacacggtcg gtaaatacaa agggttaact gatagcaccc aaccatcttt agttagagtt   32160
gagcttcgag aacaagctcg tgttgaaggt attgaggacg cttcgttgtt tatgggtggg   32220
gatgtttcta gtcttaaatt tgacaccaat atccatggga tagaatatgc taaacatcca   32280
acagagaaag gtgcagtggt cttaaaagat gggactgtta tctcagctca taatccaatc   32340
aaccctgaga caatcaaaca gttccaatcc ctacaaacat ttaatggtca gaagtttgac   32400
cctaacctaa caggtaagca taaacacgtt ggtgggttca agaagaatcg ccaagttaaa   32460 ggtatgacccc tcaaaggtaa acagaaacaa agcaaagaga cagtccaaac cgagtatcaa   32520
acaatgagtc cagaacaaca aggaaacact gtcggttatc tagataatga aatctacacg   32580
gctaacaagg gttttgactt aggtggtgtc actgagttag cttatgcacc ttttaggagc   32640
caagatgaag aagtaagggt tttagcttct gtcttaatga gaccgtccac aggtgcaact   32700
gatggtagca gtggtcttcg tggtgcaacc gttgaggata ttcttagtcg tgaaactcag   32760
ttggataatg tattttatga gaaagcttcc acactgtcta acgatgctta caagaatac   32820 cgtatggtaa ataaaggtat taataacgat acagcaacct atgaggtcaa taggaaagta   32880
gcagaagcga ttgaagaccc taataaatac gctaatctca ctcaaaaaga gaaagaacta   32940
gcggatacta ttagagacca cttacttggt aaggaagact cgttagctag cccgtctaag   33000
```

```
tacgggaaca taaacgccaa acctgtccta gagaagacta attggtctgg taagtatttc   33060
ccagctgctt tcgataaggg acgtaaggct cagttaatac acgataaagg ggcagatgtc   33120
ctcgaggatg cctacactag agctttgatg ttaaaatatg acaacggaac gtcagcacaa   33180
agggctgcca ttgaggattt ctataagtgg aaaaacaatg tggacggtct gacccgtgat   33240
gatatcctag aggaagccag aaagaacgct tatgcggtaa tcaagaacga cgagtttact   33300
attagttcga caattgatga ccagttggaa ggtcttgttg gtatcgagcg gaataacttt   33360
atggaagcaa gacaaccatt tggttatgac ggagaggtac aactaccaga cggcacatgg   33420
ttctcaccta atgatattcg taacttcgat attatgccgt tattgagtag ttacaatcgg   33480
agggtgaatg gtgatgtagc cattatggga gcaacaggta aaacaacgaa ggaactaaaa   33540
gaggaactta ttaaactaag acagaaggct cgtaattcta atgacgcgtc tttaaataaa   33600
gaagttggcg cactcgagga gtacgttaag ttagctactg gtcgtgctag acgaaaccca   33660
gacaccttat ttgagatggg cgtcaggggca gtatcttcac tatcattagt gtctaaaggg   33720
ttctatattc cattcttgaa ctactctgag attgctagta tgttcgttaa gaataaccta   33780
agtggtctct ttagaaatgt tccaattatg cgagaaatgg ttaatctttc taagaagatg   33840
actagtgagg aagtggacgg tcttcgacat gcttttattg gaaggaact taccgatgtt   33900 ttaagacctt ctctccgaaa cactctggaa aatctacgta ataaatcatc gtcatggggt   33960
atcggtaagg aagcctacgg acgggcttta tatggtacac aggaattggt cgctaggttc   34020
ccccatgtca aatggatttc gtcatggacg aaccacatta ttgattcagc gactagcggt   34080
tttgttggtg atattgtaac agaagcttta gtcaagggtg ctaaaccgtc caaatggaat   34140
acacctgaat tcagaaaggc tgctagtatc acagatgctc aatattctga tatgttacag   34200
gttattcgag accacgctgt gttacaacca gacgggacgt atgctattaa ggataaagta   34260
gcgtttagaa acgaccctcg ctcattcaat atttggcgaa tgggtgaccg tgtggctcat   34320
gagaccattc tgagaccaca taggaccgca atgcaagaca gtaaagcgta tggggctatc   34380
ggacaggcaa tcttacagtt caaaaagttc accattaaga gcttaaactc aagaacagta   34440
gaagcttttt accaagcgac taagaatgat agagctatcg aaatggcttt aaactctgtg   34500
gtctcaatgg gtctagctac gttgttctat attgctaggg ttcacgttca agccactcaa   34560
atggatgacc cacaaggtta caaagagaga gcttttgacc ccaacatgat ggtttacaat   34620
gcgactaccc gttcgtctgt ccttgctggt gctggtgtgt tgaacatctt acttggtcta   34680
ggcggtatgg atgcagccaa agagctacga acaagtatca cacctcgtga taccaaagag   34740
agtccgtatt tccatgcaga gactggacaa ggtttagcta gggatatcgc tacaaacgtg   34800
agtgaccaaa tcccagcatt aagtacagtc gggaacgctt tagcctttgg tgctaatgca   34860
gcaggttatg cggatagcac ccgtgctgtg cacgctttaa atgccttaat tggtatgaag   34920
caagctatgc aaggtgtgat gcctaatgac cctttatctc aatggttagt tagtcagtta   34980
tatgcggatg attaataata acaaagggag accttgagtg gtctctctga ttttaaatag   35040
gagacaatat gtcatcaaga gatatcagta cggtggcgac ctatcgaatc gacggttcca   35100
cagtggagtt tctgattcca ttcgagtatc ttagccgtaa attcgttagg gtcactctga   35160
ttggtagaga ccgaaaggaa ctcgttgtaa atagggatta ccgttatgta tcagttaccc   35220
aaatcagaac aactaaaact tggcaagtca gtgaaggtta tgagttcatt gaattacgtc   35280
gacacacaag tgcaaccgag cgtatcgttg atttcaaaga tggttcgatt cttcgtgcgc   35340
aagaccttaa tattagtaca atccaagcgt tacacattgc tgaggaagct cgaggtctag   35400
```

```
cagccgatac cttaggggtc aatgatgatg ggcatttaga tgctagaggt cgaaagattg   35460
taaatgtggc taacccagat tctgaccgag acgctgttaa ctttaggttc ctcgatggga   35520
ccgagaagtc agtcactcaa accctagccg aagttaagcg gttgaagcaa gatattgacg   35580
ctaaacatac acaggttggt aaagatacga acgaggtaag acaagcggtt gttactacta   35640
gtcaacataa agtcgcttct gagcaagcaa gagatcgtgc ggaaactgct gcatctcaag   35700
cggaacaatc agctaacatt gcgagcacta aagctaacca agcgagccaa tcggaacaga   35760
acgcttcaac tagtgcgtcc caagcgagcc aatcggcaac taaagcagaa caggaagcca   35820
ataaggcaca gcaggctgcc aatgaggcta tcggtggggc tattccaaac actaagaaat   35880
cagataatga taacagttca agttcagata ctgttgcaac tagttacgct gttaaaaagg   35940
tacgtgattt tgtagaaaat cgattttcat ccctcgctaa tgcggatggc tataaacatg   36000
ttggtcgttg taaatcagta gagatgttac gcaaagtcgt tcctagtaaa catggacagc   36060
gtattttggt ggatgcgtac tatgaaggca gcacaacagg cggtggtgag tttgtggcgg   36120
atttgcaaga tttaacgaca gcagatgatg gaggaagttg ttttgttgtg ttgaacaata   36180
cagcgcgttg gaaacggata tttgatgatc gtgtggatgt ggtcgatttt ggcgcaaaat   36240
cagatgaaga cgcgacaatc gcgtttgaaa atgcgtttaa atatgcgggt gagcacaaga   36300
agataattac gtctgatgcg tccacttatt tcatcaataa gccattattt ctctcgggtg   36360 ttgggggat tgaattaaac ggtaagcttt atgcgaaaat gaccccagag aacaaaagta   36420
aacccattat tacttgggca gaaaatgcga taacactcac gcaatcgcac aacaattta   36480 tcaatttcgt catgtggtta gagccgacag aggatgctcc cgcgatatgc ttagcgggtt   36540
taaaatcgac caatttaaag attggagaaa cgggctgtgt tcagctttat gcaacaacgg   36600
ataaagccga gcaacaaaga aaatttaacg gacttgatac gagttctttg gcttacaata   36660
gattcgatat cgatgttta tctactttac atattacagg caaagcagat ggttgggtaa   36720
atgaaaatgt cattaatgca caacgcttta gagcattaaa agcgggcttc cgggcaggta   36780
tactcattga tggtgagtat cgccataatc ataatttaat tagacgaggt tgtttggagg   36840
gagggcaaac gataaatatt gaaaatggct caagcaacac aattgaggat gcgcgttttg   36900
agcgtaatcc gaaaaatccg gatgagttat taacgatttc gttttcggaa aaagcctttt   36960
caaacagaat cattgcgagc tgggtatcaa gtccagaatt cacaaatacc ccctacggtg   37020
tgcattacgg tatggtgaag gtgacggata agggagtaga caatgttgta agtcatatac   37080
aagaaactta ttcagatgaa gcgtgtttat ttgccttgtc acaaacgaca tcttttggct   37140
caacggtcaa taaagcgacc tttcccatga aatacacaac ggatattgaa ggggtaaatg   37200
gtattaagca gcttattagt ggtagtttta aactgttgca aaattacgct gaagtctata   37260
aacaaagcca attcatacac gtaagaatcg gaacgatgtt tgatttaagt tcagatgcat   37320
cacacttccg tttgggagtg gaattgtttg atgaaaacaa agcaccgatt actcagcgt   37380 tagatagtca tataaaatca ggacaactca agtcgatgg aaacaaatac aagatggacc   37440
gcaatgtgag tcatgctaat tttacgatta tctctgagca ggtgcgctat gtaagggtgt   37500
taatcacttc aggaaatgat acggaaaacc aagttttga ttatttacgt tttgtggtgc   37560
gctatccgaa gcactttatt gaaaaatcga gaggatatca taatattcaa cagccgatta   37620
gaaagcgaag cttgttttat agagatgttg atggtgatat tgatatgcg gaagtgggag   37680 aaggtgtagt gtgctataaa caagatttaa gtgaaatgaa aattaactta gtccgtgtgg   37740
ctttagtgat taacaagata gtcgggaatg tgttaatcat tgagggtctt cctgtttcag   37800
```

```
ggataaaaag gcacacacaa gatagcgagc aaggttggag cttgatttat ccgcacaatg    37860
accaagagcg taagcttgtg gtggagagag tggagttttt gtcgagtgaa aaacaaacca    37920
aaattcacat acaaggcact ataccgttgg agcttagggc gggggtgagt atcgtgttga    37980
ttttaacaaa gacaaagaag ttagcatgac aatgaaatca atttgggttc gaagactgga    38040
gggttaaggt aatgtcaatt caattggact tcaacaatga agttgtaaaa gctgcgccta    38100
taattggaac cgcaggtgca gatggggtgg taaggctctt ctggggtctt gacctaaacg    38160
aatggttcta cgttttggct attctttata cagccgtaca gattgtagcg aagcttgtag    38220
atacttggct acgcttcaag aaaggtgaac caaaaggtta cacngagtga aaacaaacc    38280 aaaattcaca tacaaggcac tataccgtcg gagcttagga cggggagag tatcgtgttg     38340 attttaacaa agacaaagaa gttagcatga cgatggaacg catgtattca gcccaaatgc    38400
attatcagca atatttaaaa aggggtaaaa atggaaaaag gacaaaaagt taaactacga    38460
aatggaaaca agagaactag taacaataat aaagaggtga ttagtgtcta ttcaattaga    38520
ttttaacaac gaggtattaa aagcttcacc tatcatagga accgcgggtg cagatggggt    38580
ggcaaggctc ttctggggtc ttgacctaaa cgaatggttc tacgttttgg ctattcttta    38640
tacagccgta cagattgtag cgaagcttgt agatacttgg ctacgctaca agaaggtga    38700 accaaaaggt tacacaccta aggaggtatt ggaagatgag cgcggataac agcttactaa    38760
agttcttaga gcaactagac actgaagcag ctcgtctaat gcttcaagac ctaaaagacc    38820
cagcacgacg aacccctcag ttatacaatg cgattaacaa cttattgaat agacataagt    38880
tccaaattgc taagttacaa cctgaggggg acgtattggg aagcttagcg gaatctctaa    38940
aagacttcca gaactctgag attgaccagt cagagtacac acagtaaaca acaaggatac    39000
tttatggctt atttaaaatt tatcttcaat aagcacacag taatctggtt tctagggatg    39060
ctattagtat ccctagtgta tcacacaggc tacaaaagtg gcacagcgaa gatgcaaacg    39120
gagattcaaa atgtacacaa acgataccaa agcgaagccg aaaggctcac taaagagaag    39180
caattggcac tcaatgaggt tagtcggaag tatcaagaag atttacaaca aatcaaaaat    39240
gaagctgatt ttactatcac taatcttact aagtctaatc agcggttgta cgtcaaactc    39300
aagtcgcttc caagtgacca caacggagct tcatgtcgac caatcgttga tggtaaagcc    39360
gaacttgacg attcaactgc tagaagtctt atcgaaataa ctaaacgtgg tgacaagtgg    39420
attgaagcac ttcaagagtc attgcgacaa tgtaaaggag aaactaaatg agagaatact    39480
ataagagtac aaaatgg                                                   39497
```

*PASTEURELLA MULTOCIDA* BACTERIOPHAGE PAS-MUP-1 AND USE THEREOF FOR INHIBITING PROLIFERATION OF *PASTEURELLA MULTOCIDA*

CROSS-REFERENCE TO RELATED APPLICATIONS

This application is a U.S. National Phase Application of International Application No. PCT/KR2016/012906, filed Nov. 10, 2016, which claims priority to Korean Application No. 10-2015-0182593, filed Dec. 21, 2015, each of which are hereby incorporated by reference in their entirety.

REFERENCE TO SEQUENCE LISTING

The Sequence Listing submitted Jul. 5, 2018 as a text file named "08162_0044U1_Revised_Sequence_Listing.txt," created on Jun. 28, 2018, and having a size of 52,260 bytes is hereby incorporated by reference pursuant to 37 C.F.R. § 1.52(e)(5).

BACKGROUND OF THE INVENTION

1. Field of the Invention

The present invention relates to a bacteriophage isolated from the nature that infects and kills *Pasteurella multocida* cells, and a method for preventing and treating the infections of *Pasteurella multocida* using a composition comprising the bacteriophage as an active ingredient. More particularly, the present invention relates to a Myoviridae bacteriophage Pas-MUP-1 (Accession NO: KCTC 12706BP) that is isolated from the nature and can kill *Pasteurella multocida* cells specifically, which has a genome represented by the nucleotide sequence of SEQ. ID. NO: 1, and a method for preventing the infections of *Pasteurella multocida* and thereafter treating them using the composition comprising said bacteriophage as an active ingredient.

2. Description of the Related Art

*Pasteurella multocida* is a Gram-negative, non-motile *bacillus*, which is classified according to capsular polysaccharides into 5 types: A, B, D, E and F. In detail, *Pasteurella multocida* type A is associated with pulmonary diseases in cattle, sheep, pigs, *Pasteurella multocida* type B provokes hemorrhagic sepsis in cattle and buffalo, and *Pasteurella multocida* type D triggers atrophic rhinitis in pigs. As such, *Pasteurella multocida* gives rise to various diseases in livestock animals, thus leading to economical damages seriously in the livestock farming industry. Therefore, it is required to develop a novel procedure for preventing diseases and conditions caused by *Pasteurella multocida* in animals, and further treating the infections of *Pasteurella multocida*.

In the livestock farming industry, antibiotics are utilized a lot in order to prevent and treat the infections of *Pasteurella multocida*. However, antibiotic-resistant bacterial strains are emerging so as to continuously reduce the effectiveness of antibiotics. Moreover, such an abuse of antibiotics for animals is being prohibited under national regulations fortified. Therefore, it is currently requested to develop a novel effective procedure rather than antibiotics. Especially, environmental-friendly methods may be preferred.

Recently, the use of bacteriophages has drawn our attention as a new way of treating bacterial infections. Particularly, the reason of our high interest in bacteriophages is because bacteriophage-based treatment is a nature-friendly method. Bacteriophages are an extremely small microorganism that infects bacteria, which are called phage in short. Once bacteriophage infects bacteria, the bacteriophage is proliferated in the inside of the bacterial cell. After proliferation, the progenies destroy the bacterial cell wall to escape from the host, suggesting that the bacteriophage has the killing ability of bacteria. The bacteriophage infection is characterized by its high specificity, so that a certain bacteriophage infects only a specific bacterium. That is, the bacterium that can be infected by certain bacteriophage is limited, suggesting that bacteriophage can kill only a specific bacterium and cannot harm other bacteria. Due to this cell specificity, the bacteriophage confers antibacterial effects upon target bacteria and excludes commensal bacteria in environmental or internal conditions of animal. Conventionally, universal antibiotics for therapeutic use of bacteria affect various kinds of bacteria coincidently, which results in a lot of problems polluting environment, disturbing normal microflora in animals or the like. Fortunately, the use of bacteriophages does not affect normal microflora and the like, because of killing the target bacteria selectively. Hence, the bacteriophage may be safe and thus lessen the probability of adverse actions, compared to any other antibiotics.

Bacteriophage was first found out by an English bacteriologist Twort in 1915 when he noticed that *Micrococcus* colonies melted and became transparent by something unknown. In 1917, a French bacteriologist d'Herelle found out that *Shigella dysenteriae* in the filtrate of dysentery patient feces melted by something, and further studied about this phenomenon. As a result, he identified bacteriophage independently, and named it as bacteriophage which means a bacteria killer. Since then, bacteriophages specifically acting against such pathogenic bacteria as *Shigella, Salmonella Typhi* and *Vibrio cholerae* have been continuously identified.

Owing to the unique capability of bacteriophage to kill bacteria, bacteriophages have been studied and anticipated as a better method to treat bacterial infections. However, after penicillin was found by Fleming, studies on bacteriophages had been only continued in some of Eastern European countries and the former Soviet Union because of the universalization of antibiotics. After the year of 2000, the merit of the conventional antibiotics faded because of the increase of antibiotic-resistant bacteria. So, bacteriophages are once again spotlighted as a new antibacterial agent that can replace the conventional antibiotics. Furthermore, the recent regulation of using antibiotics is fortified by the government world-widely. The interest on bacteriophages is increasing more and also industrial applications are increasingly achieved.

As demonstrated above, bacteriophages tend to be highly specific for bacteria. The specificity often makes bacteriophages effective upon a part of bacteria, even though belonging to the same kinds. In addition, the effectiveness of bacteriophage is different, depending upon target bacterial strains. Therefore, it is necessary to collect many kinds of bacteriophages that are useful to control specified bacteria efficiently. Hence, in order to develop a use of bacteriophages for coping with *Pasteurella multocida*, a lot of bacteriophages (many kinds of bacteriophages that give an antibacterial action against *Pasteurella multocida*) should be acquired. Furthermore, the resulting bacteriophages need to be screened whether or not superior to others in respects of antibacterial strength and spectrum.

Therefore, the present inventors tried to develop a composition applicable for the prevention or treatment of *Pas-* teurella multocida infections by using a bacteriophage that is isolated from the nature and can kill *Pasteurella multocida* cells selectively, and further to establish a method for preventing or treating the infections of *Pasteurella multocida* using the composition. As a result, the present inventors isolated bacteriophages suitable for this purpose and secured the nucleotide sequence of the genome that distinguishes the bacteriophage of the present invention from other bacteriophages. Then, we have developed a composition comprising the isolated bacteriophage as an active ingredient, and confirmed that this composition could be efficiently used to prevent and treat the infections of *Pasteurella multocida*, leading to the completion of the present invention.

SUMMARY OF THE INVENTION

It is an object of the present invention to provide a Myoviridae bacteriophage Pas-MUP-1 (Accession NO: KCTC 12706BP, deposited under the Budapest Treaty on the International Procedure at the Korean Collection for Type Cultures, Korea Research Institute of Bioscience and Biotechnology (KRIBB), 125 Gwahak-ro, Yuseong-gu, Daijeon 305-806, Republic of Korea; the deposit was made on Nov. 7, 2014.) that is isolated from the nature and can kill *Pasteurella multocida* cells specifically, which has the genome represented by the nucleotide sequence of SEQ. ID. NO: 1.

It is another object of the present invention to provide a composition applicable for the prevention of *Pasteurella multocida* infections, which comprises the bacteriophage Pas-MUP-1 that can infect and kill *Pasteurella multocida* cells, as an active ingredient and a method for preventing the infections of *Pasteurella multocida* using said composition.

It is another object of the present invention to provide a composition applicable for the treatment of *Pasteurella multocida* infections, which comprises the bacteriophage Pas-MUP-1 that can infect and kill *Pasteurella multocida* cells, as an active ingredient and a method for treating the infections of *Pasteurella multocida* using said composition.

It is another object of the present invention to provide a disinfectant for preventing and treating the infections of *Pasteurella multocida* using said composition.

It is also an object of the present invention to provide a feed additive effective upon farming by preventing and treating the infections of *Pasteurella multocida* using said composition.

To achieve the above objects, the present invention provides a Myoviridae bacteriophage Pas-MUP-1 (Accession NO: KCTC 12706BP) that is isolated from the nature and can kill specifically *Pasteurella multocida* cells, which has the genome represented by the nucleotide sequence of SEQ. ID. NO: 1, and a method for preventing and treating the infections of *Pasteurella multocida* using a composition comprising the bacteriophage as an active ingredient.

The bacteriophage Pas-MUP-1 has been isolated by the present inventors and then deposited at Korean Collection for Type Cultures, Korea Research Institute of Bioscience and Biotechnology in Nov. 7, 2014 (Accession NO: KCTC 12706BP).

In addition, the present invention also provides a disinfectant and a feed additive applicable for the prevention or treatment of *Pasteurella multocida* infections, which comprises the bacteriophage Pas-MUP-1 as an active ingredient.

Since the bacteriophage Pas-MUP-1 included in the composition of the present invention kills *Pasteurella multocida* cells efficiently, it is regarded effective to prevent or treat diseases (infections) caused by *Pasteurella multocida*. Therefore, the composition of the present invention can be utilized for the prevention and treatment of diseases caused by *Pasteurella multocida*.

In this description, the term "prevention" or "prevent" indicates (i) to block the infections of *Pasteurella multocida*; and (ii) to block the development of diseases caused by *Pasteurella multocida*.

In this description, the term "treatment" or "treat" indicates (i) to suppress the diseases caused by *Pasteurella multocida*; and (ii) to relieve the condition of diseases caused by *Pasteurella multocida*.

In this description, the term "isolation" or "isolated" indicates all the actions to separate the bacteriophage by means of experimental techniques and to secure the characteristics that can distinguish this bacteriophage from others, and further includes the action of proliferating the bacteriophage by means of bioengineering techniques so as to make it useful.

The pharmaceutically acceptable carrier included in the composition of the present invention is the one that is generally used for the preparation of a pharmaceutical formulation, which is exemplified by lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, and mineral oil, but not always limited thereto. The composition of the present invention can additionally include lubricants, wetting agents, sweeteners, flavors, emulsifiers, suspending agents, and preservatives, in addition to the above ingredients.

In the composition of the present invention, the bacteriophage Pas-MUP-1 is included as an active ingredient. At this time, the bacteriophage Pas-MUP-1 is included at the concentration of $1 \times 10^1$ pfu/ml~$1 \times 10^{30}$ pfu/ml or $1 \times 10^1$ pfu/g~$1 \times 10^{30}$ pfu/g, and preferably at the concentration of $1 \times 10^4$ pfu/ml~$1 \times 10^{15}$ pfu/ml or $1 \times 10^4$ pfu/g~$1 \times 10^{15}$ pfu/g.

The composition of the present invention can be formulated by conventional methods that are conducted by those in the art with pharmaceutically acceptable carriers and/or excipients in the form of unit dose or in a multi-dose container. The formulation can be in the form of solution, suspension or emulsion in oil or water-soluble medium, extract, powder, granule, tablet or capsule and additionally, a dispersing agent or stabilizer can be included.

The composition of the present invention can be prepared as a disinfectant or a feed additive according to the purpose of use, but not always limited thereto.

For this purpose, other bacteriophages that can confer an antibacterial activity against other bacterial species can be further comprised in the composition of the present invention in order to improve its effectiveness. In addition, other kinds of bacteriophages that have an antibacterial activity against *Pasteurella multocida* can be further comprised in the composition of the present invention. Besides, these bacteriophages can be combined properly so as to maximize antibacterial effects, because their antibacterial activities against *Pasteurella multocida* can be differential in respects of antibacterial strength and spectrum.

ADVANTAGEOUS EFFECT

The method for preventing and treating the infections of *Pasteurella multocida* using this composition comprising the bacteriophage Pas-MUP-1 as an active ingredient, has the advantage of high specificity for *Pasteurella multocida*, compared with the conventional methods based on the chemical materials including the conventional antibiotics. That means, the composition of the present invention can be used for preventing or treating the infections of *Pasteurella multocida* specifically without affecting normal microflora, and accordingly has fewer side effects. In general, when chemical materials such as antibiotics are used, commensal bacteria are also damaged so as to weaken immunity in animals with carrying various side effects. In the meantime, the composition of the present invention uses the bacteriophage isolated from the nature as an active ingredient, so that it is very nature-friendly. Besides, the antibacterial activity of bacteriophages against target bacteria is different, even if belonging to the same species, in respects of antibacterial strength and spectrum (within several strains of *Pasteurella multocida*, the antibacterial range of bacteriophages contributing to every strain. Typically, bacteriophages are usually effective upon a part of bacterial strains even in the same species. That is to say, the antibacterial activity of bacteriophage is different depending on bacterial strain in spite of belonging to the same species). Then, the bacteriophage of the present invention can provide antibiotic activity against *Pasteurella multocida* different to that provided by other bacteriophages acting on *Pasteurella multocida*. Therefore, the bacteriophage of the present invention can provide different applicability for livestock industry.

BRIEF DESCRIPTION OF THE DRAWINGS

The application of the preferred embodiments of the present invention is best understood with reference to the accompanying drawings, wherein:

FIG. 1 is an electron micrograph showing the morphology of the bacteriophage Pas-MUP-1.

FIG. 2 is a photograph illustrating the capability of the bacteriophage Pas-MUP-1 to kill *Pasteurella multocida* cells. The clear zone on the dish is the formation of plaque by lysis of target bacteria cells.

DESCRIPTION OF THE PREFERRED EMBODIMENTS

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Isolation of Bacteriophage Capable of Killing *Pasteurella multocida*

Samples were collected from the nature to isolate the bacteriophage capable of killing *Pasteurella multocida*. The *Pasteurella multocida* strains used for the bacteriophage isolation herein were the strains that had been isolated by the present inventors and identified as *Pasteurella multocida* previously.

The isolation procedure of the bacteriophage is described in detail hereinafter. The collected sample was added to the TSB (Tryptic Soy Broth) medium (pancreatic digest of casein, 17 g/L; papaic digest of soybean, 3 g/L; dextrose, 2.5 g/L; sodium chloride, 5 g/L; dipotassium phosphate, 2.5 g/L) inoculated with *Pasteurella multocida* at the ratio of 1/1000, followed by shaking culture at 37° C. for 3~4 hours.

Upon completion of the culture, centrifugation was performed at 8,000 rpm for 20 minutes and supernatant was recovered. The recovered supernatant was inoculated with *Pasteurella multocida* at the ratio of 1/1000, followed by shaking culture at 37° C. for 3~4 hours. When the sample contained the bacteriophage, the above procedure was repeated total 5 times in order to sufficiently increase the titer of the bacteriophage. After repeating the procedure 5 times, the culture solution proceeded to centrifugation at 8,000 rpm for 20 minutes and the resulting supernatant was recovered. The recovered supernatant was filtered by using a 0.45 μm filter. The resulting filtrate was used in spot assay for examining whether or not the bacteriophage capable of killing *Pasteurella multocida* was included therein.

Spot assay was performed as follows; TSB medium was inoculated with *Pasteurella multocida* at the ratio of 1/1000, followed by shaking culture at 37° C. for overnight. 3 ml (1.5 of $OD_{600}$) of the culture broth of *Pasteurella multocida* prepared above was spread on the TSA (Tryptic Soy Agar; pancreatic digest of casein, 17 g/L; papaic digest of soybean, 3 g/L; sodium chloride, g/L; agar, 15 g/L) plate. The plate stood in a chamber for about 30 minutes to dry. After drying, 10 μl of the resulting filtrate was spotted directly onto the surface of the *Pasteurella multocida* lawns and dried for about 30 minutes. Following drying, the plate was incubated at 37° C. for a day and then, examined for the formation of clear zones on the surface of the bacterial lawns. If a clear zone was generated where the filtrate was dropped, it could be judged that the bacteriophage capable of killing *Pasteurella multocida* was included in the filtrate. Through the above procedure, the filtrate containing the bacteriophage having the killing ability of *Pasteurella multocida* could be obtained.

After that, the bacteriophage was isolated from the filtrate confirmed above to have the bacteriophage capable of killing *Pasteurella multocida*. The conventional plaque assay was used for the isolation of pure bacteriophage. In detail, a plaque formed in the course of the plaque assay was picked up by using a sterilized tip, which was then added to the culture solution of *Pasteurella multocida*, followed by culturing at 37° C. for 4~5 hours. Upon completion of the culture, centrifugation was performed at 8,000 rpm for 20 minutes to obtain supernatant. The recovered supernatant was inoculated with *Pasteurella multocida* culture at the ratio of 1/50, followed by culturing at 37° C. for 4~5 hours. To increase the titer of the bacteriophage, the above procedure was repeated at least 5 times. Then, centrifugation was performed at 8,000 rpm for 20 minutes to obtain supernatant. Plaque assay was performed with the obtained supernatant. In general, the pure bacteriophage isolation is not completed by one-time procedure, so the above procedure was repeated by using the plaque formed above. After at least 5 times of repeated procedure, the solution containing the pure bacteriophage was obtained. The procedure for the isolation of the pure bacteriophage was generally repeated until the generated plaques became similar in sizes and morphologies. And the final pure bacteriophage isolation was confirmed by electron microscopy. Until the pure bacteriophage isolation was confirmed by electron microscopy, the above procedure was repeated. The electron microscopy was performed by the conventional method. Briefly, the solution containing the pure bacteriophage was loaded on copper grid, followed by negative staining with 2% uranyl acetate. After drying thereof, the morphology was observed using a transmission electron microscope. The electron micrograph of the bacteriophage isolated in the present invention is presented in FIG. 1. Based on the morphological characteristics, the bacteriophage isolated above was confirmed as belonging to the family Myoviridae.

The solution containing the pure bacteriophage confirmed above proceeded to purification. The culture broth of *Pasteurella multocida* was added to the solution containing the pure bacteriophage at the volume of 1/50 of the total volume of the bacteriophage solution, followed by culturing again for 4~5 hours. Upon completion of the culture, centrifugation was performed at 8,000 rpm for 20 minutes to obtain supernatant. This procedure was repeated 5 times to obtain a solution containing enough numbers of the bacteriophage. The supernatant obtained from the final centrifugation was filtered by a 0.45 μm filter, followed by the conventional polyethylene glycol (PEG) precipitation. Particularly, PEG and NaCl were added to 100 ml of the filtrate until reaching 10% PEG 8000/0.5 M NaCl, which stood at 4° C. for 2~3 hours. Then, centrifugation was performed at 8,000 rpm for 30 minutes to obtain the bacteriophage precipitate. The resulting bacteriophage precipitate was resuspended in 5 ml of buffer (10 mM Tris-HCl, 10 mM $MgSO_4$, 0.1% Gelatin, pH 8.0). This solution was called as the bacteriophage suspension or bacteriophage solution.

As a result, the pure bacteriophage purified above was collected, which was named as the bacteriophage Pas-MUP-1 and then deposited at Korean Collection for Type Cultures, Korea Research Institute of Bioscience and Biotechnology in Nov. 7, 2014 (Accession NO: KCTC 12706BP).

Example 2

Separation and Sequence Analysis of the Bacteriophage Pas-MUP-1 Genome

The genome of the bacteriophage Pas-MUP-1 was separated as follows. The genome was separated from the bacteriophage suspension obtained in Example 1. First, in order to eliminate DNA and RNA of *Pasteurella multocida* cells included in the suspension, DNase I and RNase A were added 200 U each to 10 ml of the bacteriophage suspension, which was incubated at 37° C. for 30 minutes. 30 minutes later, to remove the DNase I and RNase A activity, 500 μl of 0.5 M ethylenediaminetetraacetic acid (EDTA) was added thereto, which was incubated for 10 minutes. The suspension was further incubated at 65° C. for 10 minutes and then added with 100 μl of proteinase K (20 mg/ml) to break the outer wall of the bacteriophage, followed by incubation at 37° C. for 20 minutes. After that, 500 μl of 10% sodium dodecyl sulfate (SDS) solution was added thereto, followed by incubation at 65° C. for 1 hour. 10 ml of the mixture of phenol:chloroform:isoamylalcohol in a ratio of 25:24:1 was added thereto, followed by mixing well. The mixture was centrifuged at 13,000 rpm for 15 minutes to separate each layer. The upper layer was obtained, to which isopropyl alcohol was added at the volume of 1.5 times the volume of the upper layer, followed by centrifugation at 13,000 rpm for 10 minutes to precipitate the genome of the bacteriophage. After collecting the precipitate, 70% ethanol was added to the precipitate, followed by centrifugation at 13,000 rpm for 10 minutes to wash the precipitate. The washed precipitate was recovered, vacuum-dried and then dissolved in 100 μl of water. This procedure was repeated to obtain a sufficient amount of the bacteriophage Pas-MUP-1 genome.

The nucleotide sequence of the genome of the bacteriophage Pas-MUP-1 obtained above was analyzed by Next Generation Sequencing (NGS) using illumina Mi-Seq device at National Instrumentation Center for Environmental Management, Seoul National University. As a result, it is suggested that the final genome of bacteriophage Pas-MUP-1 have 39,497 bp of size and the nucleotide sequence of the whole genome has SEQ. ID. NO: 1.

Based upon the genomic sequence of the bacteriophage Pas-MUP-1 obtained above, its similarity to other genomic sequences previously reported was investigated by using BLAST. From the BLAST result, it is shown that there is no genomic sequence having more than 50% homology with that of the bacteriophage Pas-MUP-1.

Based upon this result, it is concluded that the bacteriophage Pas-MUP-1 is a novel bacteriophage never reported before. Along with this result, it is referred herein that when bacteriophages are different in their kinds, their antibacterial strength and spectrum become different typically. Therefore, it is concluded that the bacteriophage Pas-MUP-1 provides different type of valuable antibacterial activity compared to other bacteriophages aforementioned.

Example 3

Investigation of Killing Ability of the Bacteriophage Pas-MUP-1 Against *Pasteurella multocida*

The killing ability of the isolated bacteriophage Pas-MUP-1 against *Pasteurella multocida* was investigated. To do so, the formation of clear zone was observed by the spot assay by the same manner as described in Example 1. The *Pasteurella multocida* used for this investigation were total 10 strains which had been isolated and identified as *Pasteurella multocida* previously by the present inventors. The bacteriophage Pas-MUP-1 demonstrated the killing ability against 9 strains of the *Pasteurella multocida* used in this experiment. The representative result of the killing ability test is shown in FIG. 2. In the meantime, the activity of the bacteriophage Pas-MUP-1 to kill *Staphylococcus aureus, Enterococcus faecalis, Enterococcus faecium, Lactobacillus plantarum, Streptococcus uberis* and *Pseudomonas aeruginosa* was also investigated in each separated test. As a result, it is found that the bacteriophage Pas-MUP-1 does not have the killing activity against these microorganisms.

Therefore, it was confirmed that the bacteriophage Pas-MUP-1 has the specific ability to kill *Pasteurella multocida* and a broad antibacterial spectrum against *Pasteurella multocida*, suggesting that the bacteriophage Pas-MUP-1 of the present invention could be used as an active ingredient of the composition for preventing and treating the infections of *Pasteurella multocida*.

Example 4

Preventive Effect of Bacteriophage Pas-MUP-1 on the Infections of *Pasteurella multocida*

100 μl of the bacteriophage Pas-MUP-1 solution at $1 \times 10^8$ pfu/ml was added to a tube containing 9 ml of TSB. To another tube containing 9 ml of TSB, only the same volume of TSB was added. Then, the *Pasteurella multocida* culture was added to each tube until $OD_{600}$ reached about 0.5. After that, the tubes were transferred to an incubator at 37° C., followed by shaking culture, during which the growth of *Pasteurella multocida* was observed. As presented in Table 1, the growth of *Pasteurella multocida* was inhibited in the tube adding the bacteriophage Pas-MUP-1 solution, while the growth of *Pasteurella multocida* was not inhibited in the tube without adding the bacteriophage Pas-MUP-1 solution.

TABLE 1

Growth inhibition of *Pasteurella multocida*

| Item | $OD_{600}$ | | |
|---|---|---|---|
| | 0 min. | 60 min. | 120 min. |
| (−) bacteriophage solution | 0.501 | 0.876 | 1.201 |
| (+) bacteriophage solution | 0.501 | 0.308 | 0.286 |

The above results indicate that the bacteriophage Pas-MUP-1 could not only inhibit the growth of *Pasteurella multocida* but also kill them. Therefore, it is concluded that the bacteriophage Pas-MUP-1 can be used as an active ingredient of the composition for preventing the infections of *Pasteurella multocida*.

Example 5

Preventive Effect of Bacteriophage Pas-MUP-1 on the Infections of *Pasteurella multocida* in Animal Model Preventive effect of the bacteriophage Pas-MUP-1 on weaning pigs affected by *Pasteurella multocida* was investigated. 4 weaning pigs at 25 days of age were grouped together; total 2 groups of pigs were raised in each pig pen (1.1 m×1.0 m). Heating system was furnished and the surrounding environment was controlled. The temperature and the humidity of the pig pen were controlled consistently and the floor was cleaned every day. From the 1$^{st}$ day of the experiment, pigs of the experimental group (adding the bacteriophage) were fed with feeds adding the bacteriophage Pas-MUP-1 at 1×10$^8$ pfu/g according to the conventional feed supply procedure, while pigs of the control group (without adding the bacteriophage) were fed with the same feed without adding the bacteriophage Pas-MUP-1 according to the conventional procedure. From the 7$^{th}$ day of the experiment, the feeds of both groups were contaminated with 1×10$^8$ cfu/g of *Pasteurella multocida* for 2 days and thereafter provided twice a day respectively for the experimental and the control groups so as to bring about the infections of *Pasteurella multocida*. From the next day after providing contaminated feeds for 2 days (the 9$^{th}$ day of the experiment), pigs of the experimental group (adding the bacteriophage) were fed again with the feeds adding the bacteriophage Pas-MUP-1 at 1×10$^8$ pfu/g without contaminating *Pasteurella multocida* according to the conventional feed supply procedure as before, while pigs of the control group (without adding the bacteriophage) were fed with the same feed without adding the bacteriophage according to the conventional procedure. From the 9$^{th}$ day of the experiment, all the test animals were examined whether *Pasteurella multocida* cells are detected in their nasal discharge or not. In detail, samples of the nasal discharge (nasal swab in the inside of nasal cavity) were smeared onto blood agar plates, incubated at 37° C. for 18~24 hours to make bacterial colonies. Then, the resulting colonies were screen to select the *Pasteurella multocida* cells. By using the colony samples selected above, polymerase chain reaction (PCR) specific for *Pasteurella multocida* was performed so as to identify *Pasteurella multocida* cells. The result is presented in Table 2.

TABLE 2

Detection of *Pasteurella multocida* (average values)

| | *Pasteurella multocida* colonies per plate (No.) | | | | | |
|---|---|---|---|---|---|---|
| | Days | | | | | |
| | D9 | D10 | D11 | D12 | D13 | D14 |
| Control group (−bacteriophage) | 15 | 14 | 16 | 15 | 14 | 13 |
| Experimental group (+bacteriophage) | 4 | 3 | 1 | 0 | 0 | 0 |

From the above results, it is confirmed that the bacteriophage Pas-MUP-1 of the present invention could be very effective to suppress the infections of *Pasteurella multocida*.

Example 6

Therapeutic Effect of Bacteriophage Pas-MUP-1 on the Infections of *Pasteurella multocida*

Therapeutic effect of the bacteriophage Pas-MUP-1 on animals affected by *Pasteurella multocida* was investigated. 4 weaning pigs at 25 days of age were grouped together; total 2 groups of pigs were raised in each pig pen (1.1 m×1.0 m). Heating system was furnished and the surrounding environment was controlled. The temperature and the humidity of the pig pen were controlled consistently and the floor was cleaned every day. On the 4$^{th}$ day of the experiment, all the pigs were sprayed to the nasal cavity with 5 ml of *Pasteurella multocida* suspension (10$^9$ cfu/ml). The *Pasteurella multocida* suspension inoculated above was prepared as follows: *Pasteurella multocida* was cultured in TSB medium at 37° C. for 18 hours and then the resulting bacterial cells were recovered. Saline (pH 7.2) was added to the bacterial cell pellet to adjust cell suspension at the concentration of 10$^9$ CFU/ml. From the next day of the *Pasteurella multocida* challenge, the experimental group (adding bacteriophage solution) was sprayed nasally with the bacteriophage Pas-MUP-1 at 10$^9$ PFU/head twice a day by the same way as used for the above administration. The control group (without adding bacteriophage solution) was treated with nothing. Feeds and drinking water were equally provided to both the groups. From the 3$^{rd}$ day after the challenge of *Pasteurella multocida* (the 7$^{th}$ day of the experiment), all the animals were examined every day whether they were suffered from atrophic rhinitis caused by *Pasteurella multocida* or not. The atrophic rhinitis caused by *Pasteurella multocida* was evaluated by detecting the presence of *Pasteurella multocida* cells within the nasal discharge as described in Example 5. The result is presented in Table 3.

TABLE 3

Detection of *Pasteurella multocida* (average values)

| | *Pasteurella multocida* colonies per plate (No.) | | | | | | | |
|---|---|---|---|---|---|---|---|---|
| | Days | | | | | | | |
| | D7 | D8 | D9 | D10 | D11 | D12 | D13 | D14 |
| Control group (−bacteriophage) | 21 | 25 | 20 | 24 | 27 | 18 | 20 | 21 |
| Experimental group (+bacteriophage) | 6 | 5 | 3 | 0 | 1 | 0 | 0 | 0 |

From the above results, it is confirmed that the bacteriophage Pas-MUP-1 of the present invention could be very effective to treat the infections of *Pasteurella multocida*.

Example 7

Preparation of Feed Additives and Feeds

Feed additives were prepared by adding the bacteriophage Pas-MUP-1 solution at the concentration of $1 \times 10^8$ pfu/g feed additives. The preparation method thereof was as follows: Maltodextrin (50%, w/v) was added to the bacteriophage solution, mixed and then freeze-dried. Lastly, the dried mixture was grinded into fine powders. The drying procedure above can be replaced with drying under a reduced pressure, drying at warm temperature, or drying at room temperature. To prepare the control, feed additives that did not contain the bacteriophage but contained only buffer (10 mM Tris-HCl, 10 mM $MgSO_4$, 0.1% Gelatin, pH 8.0) were prepared.

The above two kinds of feed additives were mixed with the volume of the 1,000 times volume of feed for pig farming respectively, resulting in two kinds of final feeds.

Example 8

Preparation of Disinfectants

Disinfectants containing bacteriophage Pas-MUP-1 at the concentration of $1 \times 10^8$ pfu/ml were prepared by using the bacteriophage Pas-MUP-1 solution. In detail, to prepare the disinfectant, the bacteriophage Pas-MUP-1 solution at the concentration of $1 \times 10^8$ pfu was added to 1 ml buffer that is used to prepare the bacteriophage solution, and then well mixed. To prepare the control, the buffer itself that is the same with that used for the bacteriophage solution was utilized.

The two kinds of disinfectants prepared above were diluted in water at the ratio of 1:1000, and then used for final disinfectants.

Example 9

Effect on Pig Farming

The effect of the feeds and the disinfectants prepared in Example 7 and Example 8 on pig farming was investigated. Particularly, this investigation was conducted by examining degrees of animal growth and clinical signs associated with atropic rhinitis. Total 40 piglets were grouped into two, and each group was composed of 20 piglets (group A: feed test group, group B: disinfectant test group). The experiment was continued for 2 weeks. Each group was divided by two sub-groups comprising 10 piglets. Then, the sub-groups were divided according to the treatment of the bacteriophage Pas-MUP-1 (sub-group-①: treated with the bacteriophage Pas-MUP-1; and sub-group-②: not-treated with the bacteriophage). The piglets used in this experiment were weaning pigs at 20 days of age. Each sub-group was raised in a separate room placed at a sufficient distance. Each sub-group was distinguished and designated as presented in Table 4.

TABLE 4

| | Sub-groups of pig farming experiment | |
|---|---|---|
| | Sub-group | |
| Item | Treated with the bacteriophage Pas-MUP-1 | Not-treated with the bacteriophage |
| Fed with feeds | A-① | A-② |
| Treated with disinfectant | B-① | B-② |

Feeds were provided according to the conventional feed supply procedure as shown in Table 4 with the feeds prepared in Example 7. Disinfectants were treated 3 times a week with taking turns with the conventional disinfectants. That is, on the day when the disinfectant of the present invention was sprayed, the conventional disinfectant was not treated. As a consequence, it is demonstrated that the sub-group treated with the bacteriophage Pas-MUP-1 should be significantly outstanding in the degree of growth, compared to the sub-group not-treated with the bacteriophage Pas-MUP-1. Also the clinical sign of atrophic rhinitis was not found in the sub-group treated with the bacteriophage Pas-MUP-1, but it was manifested in about 5% of subjects from the sub-group not-treated with the bacteriophage. Furthermore, as described in Example 5, the sub-groups were examined whether separating *Pasteurella multocida* cells from the nasal discharge or not. As a result, it is shown that the *Pasteurella multocida* cells should be detected in the nasal discharge of some animals from the sub-group not-treated with the bacteriophage, while not detected in that of all the animals from the sub-group treated with the bacteriophage Pas-MUP-1.

From the above results, it is confirmed that the feeds and the disinfectants prepared according to the present invention were effective to improve outcomes in animal farming. Therefore, it is concluded that the composition of the present invention could be efficiently applied to increase the productivity in animal farming.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for preventing or treating an infection of *Pasteurella multocida*, which comprises a step of administering to a subject a composition comprising bacteriophage Pas-MUP-1 (Accession NO: KCTC 12706BP).

2. The method for preventing or treating an infection of *Pasteurella multocida* according to claim 1, wherein said composition is administered to a subject in the form of a disinfectant or a feed additive.

* * * * *